(12) United States Patent
Wempe et al.

(10) Patent No.: US 12,025,596 B2
(45) Date of Patent: Jul. 2, 2024

(54) 6-OXO-PIPECOLIC ACID QUANTITATION BY MASS SPECTROMETRY

(71) Applicant: THE REGENTS OF THE UNIVERSITY OF COLORADO, Denver, CO (US)

(72) Inventors: Michael F. Wempe, Aurora, CO (US); Johan L. Van Hove, Castle Rock, CO (US); Curtis Coughlin, II, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 895 days.

(21) Appl. No.: 16/971,103

(22) PCT Filed: Feb. 19, 2019

(86) PCT No.: PCT/US2019/018570
§ 371 (c)(1),
(2) Date: Aug. 19, 2020

(87) PCT Pub. No.: WO2019/161383
PCT Pub. Date: Aug. 22, 2019

(65) Prior Publication Data
US 2022/0057371 A1 Feb. 24, 2022

Related U.S. Application Data

(60) Provisional application No. 62/632,379, filed on Feb. 19, 2018.

(51) Int. Cl.
*G01N 30/72* (2006.01)
*G01N 30/02* (2006.01)

(52) U.S. Cl.
CPC ... *G01N 30/7233* (2013.01); *G01N 2030/027* (2013.01); *G01N 2560/00* (2013.01); *G01N 2800/2857* (2013.01)

(58) Field of Classification Search
CPC .................................................. G01N 30/7233
See application file for complete search history.

(56) References Cited

U.S. PATENT DOCUMENTS

2015/0293072 A1   10/2015   Geigenmuller et al.

FOREIGN PATENT DOCUMENTS

WO   2013/107291 A1   7/2013
WO   2016124574 A1   8/2016

OTHER PUBLICATIONS

"Metabocard for 6-Oxopiperidine-2-carboxylic acid (HMDB0061705)", Human Metabolome Database, Sep. 14, 2021, XP055855883, retrieved at http://hmdb.ca/metabolites/HMB0061705.
Extended European Search Report issued in European Patent Application No. 19753672.5 dated Nov. 9, 2021 (11 pages).
Evans, Anne M., et al., Integrated, Nontargeted Ultrahigh Performance Liquid Chromatography/Electrospray Ionization Tandem Mass Spectrometry Platform for the Identification and Relative Quantification of the Small-Molecule Complement of Biological Systems, Anal. Chem. 2009.
International Search Report dated Jun. 18, 2019 in International Patent Application No. PCT/US2019/018570 (4 pages).
Akasaka, et al., "Synthesis of a New Dual Metalloprotease Inhibitor I. Diastereoselective Alkylation of Protected 6-Oxopipecolic Acid Esters", Chemical and Pharmaceutical Bulletin, Nov. 15, 1999, vol. 47, pp. 1525-1531 (7 pages).
Pérez et al., "Clinical, biochemical, and molecular studies in pyridoxine-dependent epilepsy. Antisense therapy as possible new therapeutic option", Epilepsia Jan. 25, 2013, vol. 54, pp. 239-248 (10 pages).
PubMed Compound Summary for CID 3014237, "6-Oxopiperidine-2-carboxylic acid", U.S. National Library of Medicine, Aug. 8, 2005, pp. 1-19 (https:/pubchem.nobi.nim.nih.gov/compound/3014237) (19 pages).
Sadilkova et al., "Simultaneous determination of alpha-aminoadipic semialdehyde, piperideine-6-carboxylate and pipecolic acid by LC-MS/MS for pyridoxine-dependent seizures and folinic acid-responsive seizures", Journal of Neuroscience Methods, Jul. 23, 2009, vol. 184, pp. 136-141 (6 pages).
Wempe et al., "Identification of a novel biomarker for pyridoxine-dependent epilepsy: Implications for newborn screening", Journal of Inherited Metabolic Disease, Jan. 21, 2019, vol. 42, pp. 565-574 (10 pages).

*Primary Examiner* — Golam M Shameem
(74) *Attorney, Agent, or Firm* — Dorsey & Whitney LLP

(57) ABSTRACT

Methods for determining the presence or amount of oxopiperidine in a biological sample using mass spectrometry. These methods may be used to efficiently and non-invasively diagnose pyridoxine dependent epilepsy (PDE) due to deficient a-aminoadipic-δ-semialdehyde (α-AASA) dehydrogenase activity due to mutations in ALDH7A1, resulting in the accumulation of $\Delta^1$-P6C, P6CH, and 6-Oxo-PIP in biological samples.

11 Claims, 12 Drawing Sheets

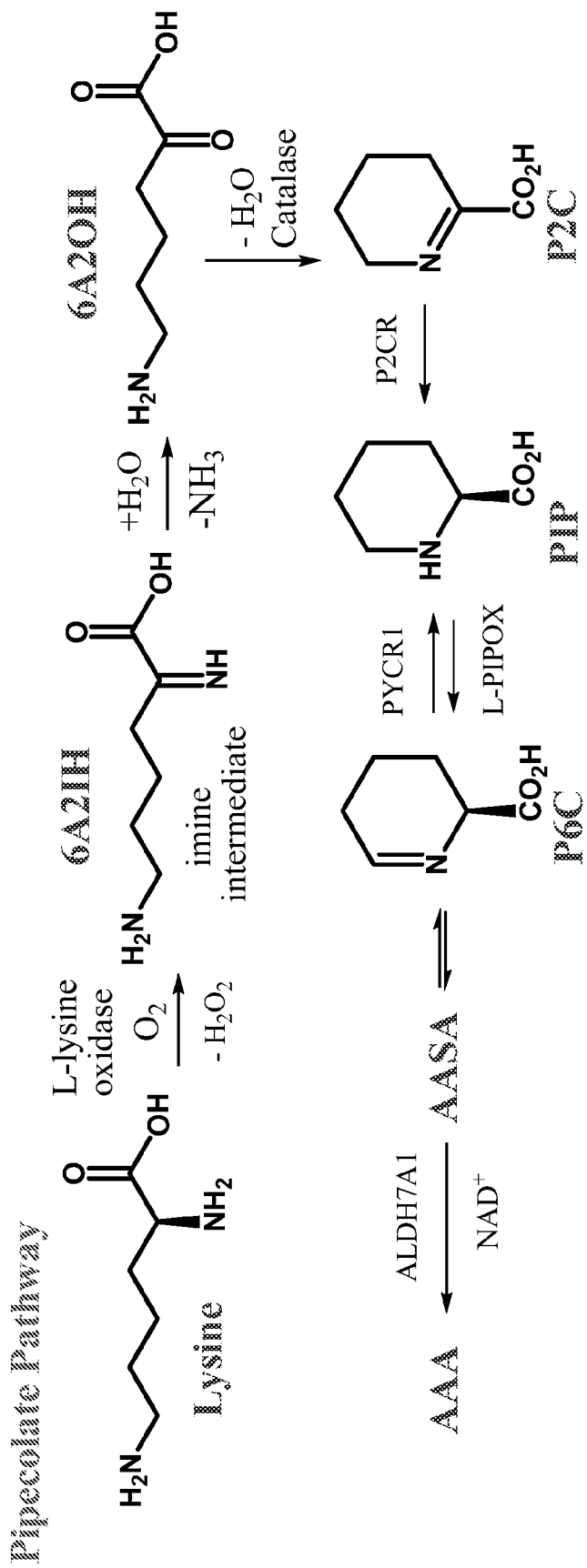
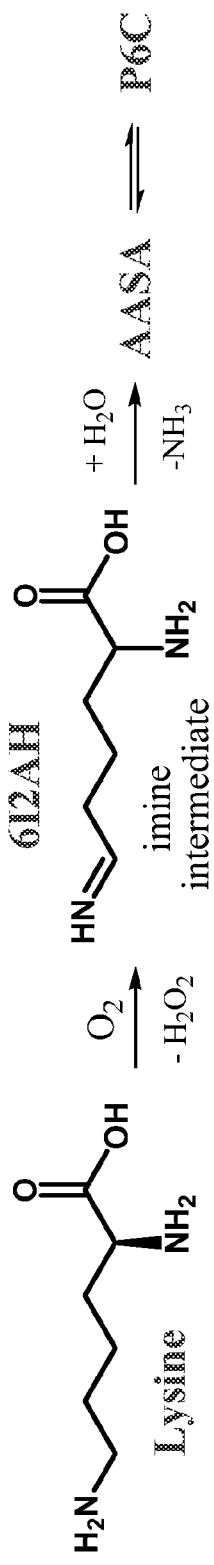
FIG. 1B
FIG. 1C

6-OXO-PIPECOLIC ACID QUANTITATION BY MASS SPECTROMETRY

CROSS-REFERENCE TO RELATED APPLICATIONS

This application is a national stage application under 35 U.S.C. § 371 of International Application No. PCT/US2019/018570, filed Feb. 19, 2019, entitled "OXOPIPERDINE QUANTITATION BY MASS SPECTROMETRY," which claims the benefit of U.S. Provisional Patent Application Ser. No. 62/632,379, filed Feb. 19, 2018, entitled "OXOPIPERIDINE QUANTITATION BY MASS SPECTROMETRY," the entire disclosures of which are incorporated herein by reference in their entirety.

STATEMENT OF FEDERALLY SPONSORED RESEARCH

This invention was made with government support under grant number UL1TR001082 awarded by the National Institutes of Health. The government has certain rights in the invention.

TECHNICAL FIELD

The invention relates to methods for quantitation of 6-oxopiperidine 2-carboxylic acid (6-oxopipecolic acid; Oxo-PIP) by mass spectrometry.

BACKGROUND

The following description of the background of the invention is provided simply as an aid in understanding the invention and is not admitted to describe or constitute prior art to the invention.

Pyridoxine dependent epilepsy (PDE) is a treatable epileptic encephalopathy, which responds readily to pyridoxine treatment. Despite adequate seizure control, seventy-five percent of individuals with PDE have significant intellectual disability and developmental delay. PDE is caused by biallelic mutations in α-aminoadipic-δ-semialdehyde (α-AASA) dehydrogenase encoded by the gene ALDH7A1 (Aldehyde Dehydrogenase 7 Family, member A1; Antiquitin-1). α-AASA dehydrogenase deficiency results in the accumulation of α-AASA and $\Delta^1$-piperidine-6-carboxylate ($\Delta^1$-P6C), which are reported to be in equilibrium. α-AASA dehydrogenase is both a mitochondrial and a cytosolic dehydrogenase and catalyzes α-AASA oxidation via nicotinamide adenine dinucleotide ($NAD^+$) to produce 2-aminoadipic acid (AAA). This α-AASA to AAA biotransformation is therefore a crucial step along the lysine oxidation pathway. There are two lysine degradation pathways that converge at α-AASA: i) the saccharopine pathway (FIG. 1A), and ii) the pipecolate pathway (FIG. 1B). The saccharopine pathway is the predominant lysine oxidation pathway in humans, particularly present in liver and kidney (FIG. 1A). This pathway utilizes two enzymatic activities coupled on a single bi-functional polypeptide known as α-aminoadipic-δ-semialdehyde synthase (AASS). Catalyzed by the lysine ketoglutarate reductase (LKR) domain, lysine couples with 2-oxoglutarate to afford an imine intermediate, which gets reduced to produce saccharopine (SAC). The second step involves the saccharopine dehydrogenase (SDH) domain which converts saccharopine to α-AASA and glutamate via the presumed imine intermediate SACI. SACI can be envisioned to react with water to generate α-AASA. Also, SACI could undergo intramolecular attack of the saccharopine amino acid amine followed by elimination of glutamate to give $\Delta^1$-P6C. As α-AASA and $\Delta^1$-P6C are reported to be in equilibrium, $\Delta^1$-P6C will subsequently ring open to afford α-AASA and become oxidized to AAA via ALDH7A1.

The pipecolate pathway (FIG. 1B) may occur via oxidation with L-lysine α-oxidase (EC 1.4.3.14) to produce the presumed intermediate 6-amino-2-iminohexanoic acid (6A2IH) with hydrogen peroxide ($H_2O_2$) production. As $H_2O_2$ is consumed, the 6-amino-2-oxo-hexanoic acid (6A2OH; 2-oxo-lysine) formed will spontaneously cyclize and dehydrate (loss of water) to give $\Delta^1$-piperideine-2-carboxylate ($\Delta^1$-P2C). Alternatively, 6A2IH could directly undergo intramolecular cyclization with loss of ammonia to produce $\Delta^1$-P2C. Second, the action of an aminotransferase on lysine converts it directly into 2-oxo-lysine, which then produces $\Delta^1$-P2C. $\Delta^1$-P2C is next reduced to L-pipecolic acid (PIP; piperidine-2-carboxylic acid) via $\Delta^1$-piperideine-2-carboxylate reductase (P2CR), a reductase found in mammalian brain. PIP is oxidized via L-pipecolate oxidase (L-PIPDX; EC 1.5.3.7) in peroxisomes to give $\Delta^1$-piperideine-6-carboxylate $\Delta^1$-P6C and $H_2O_2$. The pipecolate pathway is reported to predominate in brain, where both enzymes P2CR and L-PIPDX are predominantly expressed. $\Delta^1$-P6C and α-AASA are reported to be in equilibrium, and α-AASA becomes oxidized to AAA via α-AASA dehydrogenase.

In an analogous fashion, lysine can be oxidized at the terminal amine by L-lysine-ε-aminotransferase (LAT; FIG. 1C), which produces an imine intermediate 6-imino-2-amino-hexanoic acid (6I2AH) and subsequent addition of water with elimination of $NH_3$ affords the aldehyde α-AASA, whereas intramolecular cyclization with subsequent elimination of ammonia directly produces $\Delta^1$-P6C. The relevance of this ε-oxidation pathway in humans is not clear. Further, $\Delta^1$-P6C can be converted backwards into PIP via pyrroline-5-carboxylate reductase (PYCR1). Thus, both the pipecolate pathway and the saccharopine pathway converge at PIP, and $\Delta^1$-P6C/α-AASA, followed by α-AASA oxidation to AAA via α-AASA dehydrogenase.

To diagnose PDE, α-AASA and $\Delta^1$-P6C are detected and quantified from blood, plasma, or urine samples. To detect these molecules, research groups and clinical diagnostic laboratories derivatized using FMOC (9-Fluorenylmethoxycarbonyl chloride) or butanolic HCl to prepare butyl esters, followed by liquid chromatography tandem mass spectrometry (LC/MS-MS) analysis (S. Jung, et al., Mol. Genet. Metab. (2013) 110:237-40; T. Yuzyuk, et al., J. Chromatogr. B Analyt. Technol. Biomed. Life Sci. (2016) 1017:145-52). This derivatization scheme is slow and costly. Therefore, a faster, more accurate, and less expensive detection methodology is desired.

SUMMARY

The present inventors have surprisingly discovered that the acid catalyzed acetal deprotection from L-allysine ethylene acetal does not produce $\Delta^1$-P6C/α-AASA as previously reported (E. A. Struys, E. A., et al., J. Inherit. Metab. Dis. (2012) 35:909-16), but rather a $\Delta^1$-P6C/P6CH mixture in an approximate 2:1 ratio, which is in a dual equilibrium with $\Delta^2$-P6C. They have also demonstrated that the AASS enzyme in the saccharopine pathway produces P6CH. They have therefore determined that P6CH is the primary substrate for α-AASA dehydrogenase, can also be oxidized by a cytosolic enzyme to 6-oxo-PIP, but cannot be readily metabolized to AAA (see FIG. 4). In PDE patients, this results in the accumulation of 6-oxo-PIP, which is stable at room temperature and can be detected and quantified using stable isotope dilution liquid chromatography, tandem mass spectroscopy (LC-MS/MS). 6-oxo-PIP therefore represents a novel biomarker for PDE with characteristics that make it particularly useful in diagnostic methods.

The inventors have developed and validated an analytical method for quantitation of Oxo-PIP in a sample by mass spectrometry, including tandem mass spectrometry.

Thus, methods are provided for determining the amount of Oxo-PIP in a test sample. These methods may be used to diagnose or monitor PDE in a patient diagnosed with or suspected of having PDE. In these diagnostic methods, any appropriate method may be used to determine the amount of Oxo-PIP in a test sample from an individual. These detection/quantification methods may include mixing the test sample with an internal standard, which may be a deuterated internal standard molecule, including, for example one or both of DL-2-Amino-1,6-hexanedioic-2,5,5-$d_3$ Acid (D3-AAA) and deuterated Oxo-PIP ($D_3$-Oxo-PIP).

In these methods, the test sample may be applied directly to liquid chromatography tandem mass spectrometer (LC-MS/MS) to determine the presence or concentration of Oxo-PIP in the sample. These methods may also include mixing the test sample with a solvent, which solvent may include one or both of an alcohol such as methanol, and acetonitrile. These methods may also include mixing, such as by vortexing, and centrifuging the mixture of the test sample and the solvent to obtain a supernatant liquid, which supernatant liquid is analyzed by LC-MS/MS. These methods for determination of Oxo-PIP are less expensive and less time consuming than the methods of detecting α-AASA and/or $\Delta^1$-P6C by derivatization using FMOC or butanolic HCl. For example, the methods of this disclosure can have a run time of less than 5 minutes.

Thus, this disclosure provides methods for detection of 6-oxopiperidine-2-carboxylic acid (Oxo-PIP) in a sample, by introducing an internal standard into a sample received from a patient and, analyzing the sample containing the internal standard using liquid chromatography tandem mass spectrometer (LC-MS-MS) to determine the Oxo-PIP concentration present in the sample. In these methods, at least one alcohol and/or organic solvent may be added to the sample containing the internal standard prior to analyzing by LC-MS-MS. In this way, the sample may be mixed and centrifuged to form a supernatant in the mixture, and a portion or aliquot of the supernatant may be recovered and applied to the LC for the LC-MS-MS analysis.

In these methods, the internal standard may be a deuterated internal standard, for example, the internal standard may be deuterated Oxo-PIP ($D_3$-Oxo-PIP).

In these methods, the sample may be a biological fluid selected from saliva, sweat, urine, blood, serum, plasma, cerebrospinal fluid (CSF), and combinations thereof.

These methods may involve the combination of LC with mass spectrometry. The mass spectrometry may be tandem mass spectrometry (MS/MS). In these methods, the transitions for Oxo-PIP in mass spectra with tandem mass spectrometer are at 144.2 to 98.1. In these methods, the liquid chromatography tandem mass spectrometer (LC-MS-MS) may comprise electrospray ionization (ESI) MS. In these methods, the presence or amount of Oxo-PIP ions is related to the presence or amount of Oxo-PIP in the original test sample by comparison to a reference Oxo-PIP sample.

This disclosure also provides methods of diagnosing or monitoring pyridoxine dependent epilepsy (PDE) by obtaining a sample from a human patient and detecting whether Oxo-PIP is present in the sample. The patient is diagnosed with PDE when the presence of Oxo-PIP is detected in the sample.

This disclosure also provides methods of diagnosing and treating PDE in a patient by obtaining a sample from a human patient, and detecting whether Oxo-PIP is present in the sample. The patient is diagnosed with PDE when the presence of Oxo-PIP in the plasma sample is detected. The patient diagnosed with PCE may be treated by administering an effective amount of vitamin B6 to the diagnosed patient.

This disclosure also provides a method of monitoring the presence or progression of PDE in a patient, by obtaining a sample from a human patient and detecting the concentration of Oxo-PIP in the sample. A therapeutic change to a PDE treatment is administered to the patient if the concentration of Oxo-PIP is detected in the sample is greater than 100 μmol/mg creatinine. In these methods, the therapeutic change administered to the patient may comprise an administration of Vitamin B6. Alternatively or additionally, the therapeutic change administered to the patient may comprise administration or imposition of dietary restrictions of lysine in the patient's diet.

The summary of the invention described above is non-limiting and other features and advantages of the invention will be apparent from the following detailed description of the invention, and from the claims.

BRIEF DESCRIPTION OF FIGURES

FIGS. 1A-1C show lysine degradation pathways: FIG. 1A: the saccharopine pathway, FIG. 1B: the pipecolate pathway, and FIG. 1C: the L-lysine-e-aminotransferase pathway.

FIG. 10A shows a 21-day stability study, and FIG. 10B shows a 4-month stability study.

DETAILED DESCRIPTION

Figure 1A:
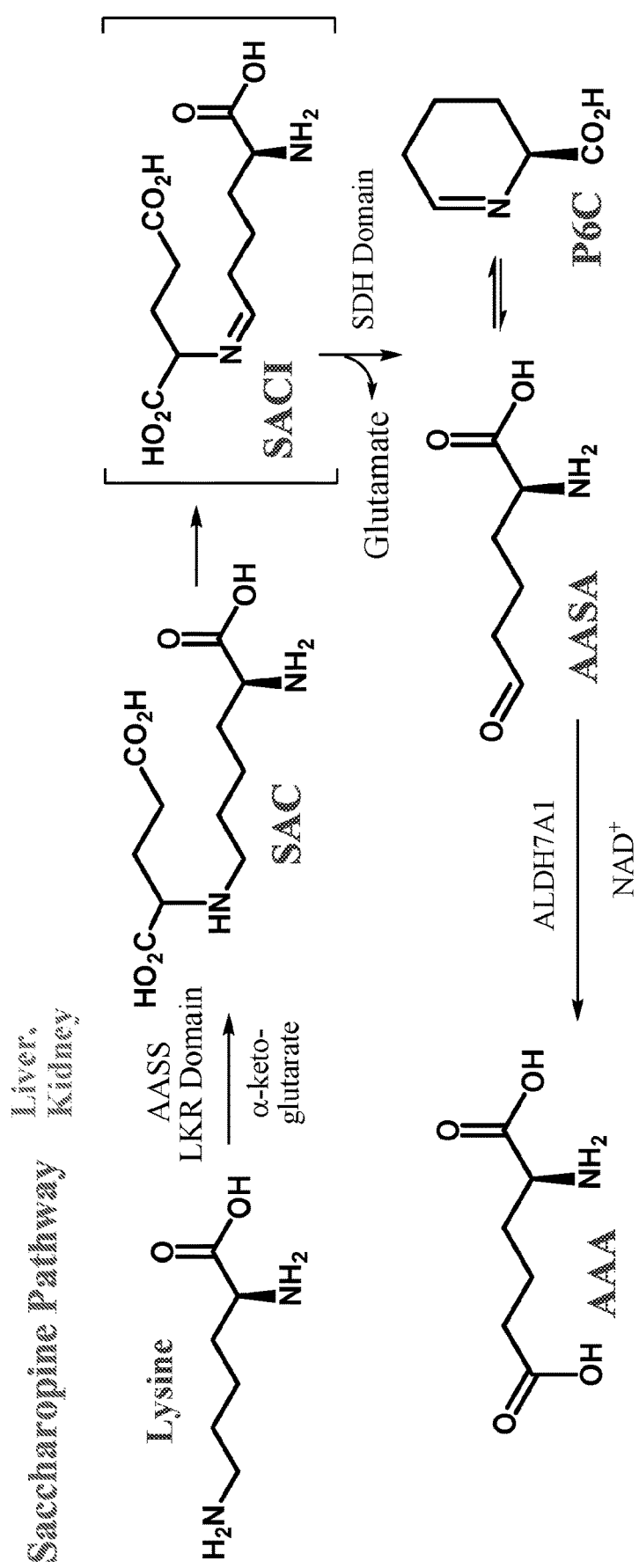

Methods are described for quantitatively measuring Oxo-PIP in a test sample. This quantitative measurement may be achieved through the use of LC-MS/MS techniques.

The materials and methods described herein can be understood more readily by reference to the following detailed description of specific aspects of the disclosed subject matter and the Examples and Figures included therein.

The aspects described below are not limited to specific synthetic methods or specific reagents, as such may, of course, vary. It is also to be understood that the terminology used herein is for the purpose of describing particular aspects only and is not intended to be limiting.

Definitions

The term "accuracy" is art-recognized and describes the degree of conformity of a measure, i.e., the quantity, to a standard or a true value. For example, an increase in the accuracy of analyte quantification refers to an improvement in obtaining a measured value that is closer to the actual or true value. This improvement may be identified/described by reference to a percent increase in accuracy with respect to the accuracy obtainable using existing methods of measurement.

The term "analyte" refers to any chemical or biological compound or substance that is subject to the analysis of the disclosure. Analytes can include, but are not limited to, small organic compounds, amino acids, peptides, polypeptides, proteins, nucleic acids, polynucleotides, biomarkers, synthetic or natural polymers, or any combination or mixture thereof. An exemplary analyte is Oxo-PIP.

The term "analyzing" or "analysis" refers to a method by which the quantity of each of the individual analytes described herein is detected. Such analysis may be made using any technique that distinguishes between the analyte (or analyte derivative) and the analyte standard (or analyte derivative standard). The analysis or act of analyzing may include liquid chromatography-tandem mass spectrometry (LC-MS-MS).

The term "chromatographic separation" is art-recognized, and describes a process in which a chemical mixture carried by a liquid or gas is separated into components as a result of differential distribution of the solutes as they flow around or over a stationary liquid or solid phase. For example, chromatographic separations suitable for use in the methods of this disclosure can include, but are not limited to liquid chromatographic (including HPLC) methods such as normal-phase HPLC, RP-HPLC, HILIC, and size-exclusion chromatography (SEC), including gel permeation chromatography (GPC). Other suitable methods include additional HPLC methods and related liquid chromatographic techniques, including, e.g., ultra-performance liquid chromatography (HPLC), fast performance liquid chromatography (FPLC) and the like.

The term "internal standard," refers to a collection of one or more functionalized chemical or biological compounds or substances, e.g., one or more analytes functionalized with another moiety in order to convert such compounds or substances into a derivative thereof. The internal standards are present in known concentrations and added to the sample to form a sample mixture. The addition of the internal standard allows for the detection of and comparison between the known concentrations of one or more known analytes, with the unknown concentrations of analytes in the original sample. As such, the internal standards can provide a way to measure the absolute quantity of an analyte in sample using a response factor calculation. Exemplary internal standards include deuterated versions of analytes to be detected in analyzed samples.

The term "liquid chromatography" is art-recognized and includes chromatographic methods in which compounds are partitioned between a liquid mobile phase and a solid stationary phase. Liquid chromatographic methods are used for analysis or purification of compounds. The liquid mobile phase can have a constant composition throughout the procedure (an isocratic method), or the composition of the mobile phase can be changed during elution (e.g., a gradual change in mobile phase composition such as a gradient elution method).

The term "mass spectrometry" and "mass spectroscopy" are art-recognized and used interchangeably to describe an instrumental method for identifying the chemical constitution of a substance by means of the separation of gaseous ions according to their differing mass and charge. A variety of mass spectrometry systems can be employed to analyze the analyte molecules of a sample subjected to the disclosed methods. For example, mass analyzers with high mass accuracy, high sensitivity and high resolution may be used and include, but are not limited to, atmospheric chemical ionization (APCI), chemical ionization (CI), electron impact (EI), fast atom bombardment (FAB), field desorption/field ionization (FD/FI), electrospray ionization (ESI), thermospray ionization (TSP), matrix-assisted laser desorption (MALDI), matrix-assisted laser desorption time-of-flight (MALDI-TOF) mass spectrometers, ESI-TOF mass spectrometers, and Fourier transform ion cyclotron mass analyzers (FT-ICR-MS). In addition, it should be understood that any combination of MS methods could be used in the methods described herein to analyze an analyte in a sample. In certain embodiments, the MS technique used for analysis of the analyte described herein is one that is applicable to most polar compounds, including amino acids, e.g., ESI.

The term "mobile phase" is art-recognized, and describes a solvent system (such as a liquid) used to carry a compound of interest into contact with a solid phase (e.g., a solid phase in a solid phase extraction (SPE) cartridge or HPLC column) and to elute a compound of interest from the solid phase.

The term "precision" is art-recognized and describes the reproducibility of a result. It is measured by comparison of successive values obtained for a measurement to the prior values, where more precise measurements (or those with greater precision) will be demonstrated by successive measurements that are more consistently closer to the prior measurements.

The terms "quantitative" and "quantitatively" are art-recognized and refers to measurements of quantity or amount. For example, the term "quantification" describes the act of measuring the quantity or amount of a particular object, e.g., an analyte. In some embodiments, the quantitative analysis can be a measurement of an absolute amount, as opposed to relative amount, i.e., the total amount of analyte may be quantified absolutely in order to determine the actual amount of the analyte.

The term "sample" refers to a representative portion of a larger whole or group of components that are capable of being separated and detected by the disclosed methods. Exemplary samples include chemically or biologically derived substances, e.g., analytes of the disclosed methods. In the analytical methods of this disclosure, the components of the sample may include, but are not limited to, small organic compounds, amino acids, peptides, polypeptides, proteins, nucleic acids, polynucleotides, biomarkers, synthetic or natural polymers, or any combination or mixture thereof. For example, the term "test sample" may refer to any sample that may contain Oxo-PIP. The term "body fluid or tissue" means any fluid or tissue that can be isolated from the body of an individual. For example, "body fluid or tissue" may include blood, plasma, CSF, serum, bile, saliva, urine, tears, perspiration, and the like. If solid tissue is to be analyzed, it may be processed to release a liquid fraction that could contain any Oxo-PIP present in the tissue. The liquid fraction can then be subject to the methods described herein.

The term "sample mixture," refers to the resultant product when a sample is mixed or combined with one or more analyte derivative standards, e.g., of a known concentration.

The term "purification" or "purifying" does not refer to removing all materials from the sample other than the analyte(s) of interest. Instead, purification refers to a procedure that enriches the amount of one or more analytes of interest relative to one or more other components of the sample. Purification, as used herein, does not require the isolation of an analyte from all others. In preferred embodiments, a purification step or procedure can be used to remove one or more interfering substances, e.g., one or more substances that would interfere with the operation of the instruments used in the methods or substances that may interfere with the detection of an analyte ion by mass spectrometry.

The term "about" in reference to quantitative measurements, not including the measurement of mass of an ion, refers to the indicated value plus or minus 10%.

The term "substantially all" refers to any proportion greater than 50%, more preferably greater than 60%, more preferably greater than 70%, more preferably greater than 80%, and more preferably greater than 90%.

"Oxo-PIP" means an intact (S)-6-oxopiperidine-2-carboxylic acid (6-oxopipecolic acid) molecule.

The term "size separation technique" means any technique (physical or chemical) that allows for the separation of at least one species from a test sample based on any one or more of molecular weight and shape. Examples of such techniques include, but are not limited to, filtration, chromatography, and certain aspects of mass spectrometry.

The term "operating in positive ion mode" refers to those mass spectrometry methods where positive ions are detected. Similarly, the term "operating in negative ion mode" refers to those mass spectrometry methods where negative ions are detected.

The term "ionization" or "ionizing" refers to the process of generating an analyte ion having a net electrical charge equal to one or more electron units. Positive ions are those having a net positive charge of one or more electron units. Negative ions are those having a net negative charge of one or more electron units.

The term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

The term "chemical ionization" or "CI" refers to methods in which a reagent gas (e.g. ammonia) is subjected to electron impact, and analyte ions are formed by the interaction of reagent gas ions and analyte molecules.

The term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

The term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization" or "ESI" refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated nitrogen gas may be used to improve removal of solvent. The gas-phase ionization in APCI can be more effective than ESI for analyzing less-polar species.

The term "Atmospheric Pressure Photoionization" or "APPI" as used herein refers to the form of mass spectrometry where the mechanism for the photoionization of molecule M is photon absorption and electron ejection to form the molecular M+. Because the photon energy typically is just above the ionization potential, the molecular ion is less susceptible to dissociation. It may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+.

The term "inductively coupled plasma" or "ICP" refers to methods in which a sample is interacted with a partially ionized gas at a sufficiently high temperature to atomize and ionize most elements As used, herein, the term "field desorption" refers to methods in which a non-volatile test sample is placed on an ionization surface, and an intense electric field is used to generate analyte ions.

The term "desorption" refers to the removal of an analyte from a surface and/or the entry of an analyte into a gaseous phase.

The term "limit of quantification" or "LOQ" refers to the point where measurements become quantitatively meaningful. The analyte response at this LOQ is identifiable, discrete and reproducible with a precision of 20% and an accuracy of 80% to 120%.

As noted above, the inventors have surprisingly discovered that the acid catalyzed acetal deprotection from L-allysine ethylene acetal does not produce $\Delta^1$-P6C/$\alpha$-AASA, but rather a $\Delta^1$-P6C/P6CH mixture in an approximate 2.1 ratio, which is in a dual equilibrium with $\Delta^2$-P6C. The relative ratio between $\Delta^1$-P6C/P6CH and $\Delta^2$-P6C was a function of the conditions used to prepare the samples. Additionally, the AASS enzyme in the saccharopine pathway also produced P6CH. P6CH is therefore the primary substrate for $\alpha$-AASA dehydrogenase and can be oxidized by a cytosolic enzyme to 6-oxo-PIP, but P6CH cannot be readily metabolized to AAA (see, FIG. 4). In PDE patients, the ability to ring open P6CH to $\alpha$-AASA or its subsequent oxidation becomes deficient, and thus does not lead to AAA. The accumulating P6CH leads to elevated levels of $\Delta^1$-P6C, as $\Delta^1$-P6C and P6CH are in equilibrium. $\Delta^1$-P6C reduction produces PIP, which is also elevated in PDE patients compared to control. P6CH is also metabolized via the minor oxidation pathway of the alcohol to produce 6-oxo-PIP, but 6-oxo-PIP does not readily hydrolyze to produce AAA, resulting in the accumulation of 6-oxo-PIP in PDE patients. Biological samples (such as blood, urine, and CSF samples) form PDE patients show evidence for both $\Delta^1$-P6C/P6CH, and 6-Oxo-PIP. Additionally, CSF samples contained small amounts of $\Delta^2$-P6C, and pipecolate pathway specific metabolites $\Delta^1$-piperideine-2-carboxylate and its hydrate. These studies have therefore identified new metabolite biomarkers never before associated with PDE. Moreover, 6-Oxo-PIP represents a very useful biomarker for PDE with characteristics of much greater stability at room temperature, which will be essential for the development of mass screening programs to timely detect patients with PDE.

The inventors have developed analytical methods for detection and quantification of this new Oxo-PIP biomarker using chromatography and mass spectrometry. In exemplary embodiments, the quantification of Oxo-PIP may be made by stable isotope dilution LC-MS/MS.

Quantitative studies often require the most sensitive means of detection possible. The MS platform and analysis mode best suited for a particular analysis needs to be determined empirically and will depend on the molecule and matrix involved. However, in general, a triple quadrupole (TQ) operated in the multiple reaction monitoring (MRM)-MS (also known as selective reactive monitoring (SRM), but also referred to as MRM) mode will show exceptional levels of sensitivity and selectivity when coupled to LC. In this mode of operation, a precursor ion is preselected and resolved in Q1 of the TQ, fragmented by collision-induced dissociation (CID) in Q2 and the resultant product ion is analyzed in Q3. Under optimal operating conditions, the precursor to product ion 'reaction' is monitored many times per second, resulting in extremely reproducible chromatographic peak shapes and intensity. In this way, a stable (heavy) isotope-labeled standard is used in stable-isotope dilution (SID) LC-MRM-MS to establish the presence of an endogenous analyte using both the LC retention time and MS/MS mass selection of the TQ platform. This level of specificity cannot be attained with any other bioanalytical technique employed for biomarker analysis.

GC- and LC-MS/MS are the two most widely used instrument platforms to employ stable-isotope dilution (SID) methodology, although LC-MS/MS is more applicable to the analysis of a wider range of biomarkers than GC-MS/MS and is also inherently easier to use for rigorous validation.

An authentic stable isotope-labeled analog of a compound is identical to the endogenous molecule except for mass. The term SID most often refers to the use of a stable isotope labeled internal standard spiked into a sample at a known concentration. The response ratio between the analyte and labeled compound can then be interpolated onto a standard curve to calculate the absolute amount of analyte in the test sample.

The analysis of small-molecule biomarkers using LC-MS/MS-based methodology most often involves the use of reversed-phase chromatography coupled to a TQ mass spectrometer or ion trap, utilizing an atmospheric pressure ionization (API) source such as electrospray ionization (ESI), nanospray or atmospheric pressure chemical ionization (APCI).

This disclosure therefore provides methods for detection and/or determination of Oxo-PIP from a sample. The sample can be a body fluid. For example, the sample can be a bodily fluid selected from the group consisting of oral fluids (saliva), sweat, urine, blood, serum, plasma, spinal fluid (CSF), and combination thereof.

These methods include mixing the sample with an internal standard. Analysis can be done using liquid chromatography tandem mass spectrometer (LC-MS-MS) to determine the Oxo-PIP concentration present in the sample. These methods may include the addition of a solvent to the test sample, as well as centrifuging the mixture to obtain a supernatant liquid. The supernatant may then be transferred to a vial, such as an auto-sampler vial for analysis. These methods may also include diluting the supernatant liquid with a mobile phase to form a solution and analyzing the solution.

In some methods, highly selective and specific methods for detection or determination of Oxo-PIP in a sample may include the steps of mixing (or "spiking") the sample with an internal standard, diluting the spiked sample with mobile phase to form a solution, and analyzing the solution using for example, liquid chromatography tandem mass spectrometer (LC-MS/MS) to determine the to determine the presence or quantity of Oxo-PIP present in the sample.

In related methods, a highly selective and specific method for detection or determination of Oxo-PIP in a sample includes the steps of mixing (or "spiking") a sample with an internal standard, mixing the sample with a solvent, centrifuging the mixture of sample and solvent to obtain a supernatant liquid, diluting the supernatant liquid with mobile phase to form a solution, and analyzing the solution using for example, liquid chromatography tandem mass spectrometer (LC-MS/MS) to determine the presence or quantity of Oxo-PIP present in the sample. Useful solvents for use in these methods may include alcohols, such as methanol (MeOH), or acetonitrile (ACN), or mixtures thereof.

In these methods, the internal standard can be selected from the group of compounds whose structure is closely related to Oxo-PIP such as deuterated Oxo-PIP ($D_3$-Oxo-PIP).

In these methods, the LC-MS/MS can include matrix-assisted laser desorption/ionization (MALDI) time-of-flight (TOF) MS analysis or electrospray ionization (ESI) MS. For example, the amount of Oxo-PIP in a sample can be determined using LC-MS/MS, and the transitions for Oxo-PIP in mass spectra with tandem mass spectrometer are at 144.2 to 98.1.

In these methods, the sample, such as a saliva sample, a blood sample, a serum sample, a plasma sample, or a urine sample is obtained from a subject, such as a human subject. In some embodiments, the subject is an epileptic subject, including a subject that has been diagnosed with or is suspected of having PDE.

Thus, this disclosure provides methods for detecting and/or determining the amount of Oxo-PIP in a sample of plasma, blood, urine, and/or CSF. These methods can include spiking the sample with an internal standard compound, such as deuterated Oxo-PIP, to form a mixture and detecting the amount of Oxo-PIP and the internal standard using LC-MS/MS.

These methods for detecting and/or determining the amount of Oxo-PIP in bodily fluid samples may include detection by electrospray tandem mass spectrometry. These methods may include determining the amount of Oxo-PIP and/or an internal standard in the sample using mass spectrometry (MS) analysis or electrospray ionization (ESI) MS.

These methods may have one or more advantages, including, for example, these methods may not require pretreatment or derivatization, the methods are highly selective towards determination of total Oxo-PIP, the methods have high throughput potential, the methods are less expensive and less time consuming than methods of detecting and quantifying α-AASA and $\Delta^1$-P6C using FMOC or butanolic HCl derivatization, these methods have less margin for introducing variations, and this prevents errors into the procedure of determination of Oxo-PIP.

Detection and Quantitation by Mass Spectrometry

Oxo-PIP may be ionized by any method known to the skilled artisan. Mass spectrometry is performed using a mass spectrometer, which includes an ion source for ionizing the fractionated sample and creating charged molecules for further analysis.

Ionization sources used in various MS techniques include, but are not limited to, electron ionization, chemical ionization, electrospray ionization (ESI), photon ionization, atmospheric pressure chemical ionization (APCI), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Oxo-PIP is preferably ionized by electrospray ionization (ESI) creating Oxo-PIP precursor ions. Oxo-PIP precursor ions are preferably in a gaseous state and the inert collision gas is argon.

After the sample has been ionized, the positively charged ions may be analyzed to determine m/z. Suitable analyzers for determining m/z include quadrupole analyzers, ion trap analyzers, and time-of-flight analyzers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM). Preferably, ions are detected using SRM.

Preferably, m/z is determined using a quadrupole instrument. In a "quadrupole" or "quadrupole ion trap" instrument, ions in an oscillating radio frequency field experience a force proportional to the DC potential applied between electrodes, the amplitude of the RF signal, and m/z. The voltage and amplitude may be selected so that only ions having a particular m/z travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to those of skill in the art. Additionally, multiple mass spectrometry steps may be combined in methods known as tandem mass spectrometry, "MS/MS". Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 400 to 1600 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples and a standard curve constructed based on ions generated from those standards. Using such a standard curve, the relative abundance of an Oxo-PIP ion may be converted into an absolute amount of the original molecule. In certain preferred embodiments, an internal standard (such as a deuterated Oxo-PIP molecule) is used to generate a standard curve for calculating the quantity of Oxo-PIP. Methods of generating and using such standard curves are well known in the art and one of ordinary skill is capable of selecting an appropriate internal standard. Numerous other methods for relating the amount of an ion to the amount of the original molecule will be well known to those of ordinary skill in the art.

One or more steps of the methods may be performed using automated machines. For example, one or more purification steps may be performed on-line, and preferably all of the GC or LC purification and mass spectrometry steps may be performed in an on-line fashion.

Techniques such as MS/MS may be used to isolate precursor ions for further fragmentation. Collision activation dissociation (CAD) may be used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy. Alternatively, electron transfer dissociation (ETD) may be used to generate the fragment ions.

Oxo-PIP may be detected and/or quantified using LC-MS/MS as follows. An Oxo-PIP enriched test sample prepared as described above is subjected to LC. The flow of liquid solvent from the chromatographic column enters the heated nebulizer interface of a LC-MS/MS analyzer and the solvent/analyte mixture is converted to vapor in the heated tubing of the interface. The analyte (e.g., Oxo-PIP), contained in the nebulized solvent, is ionized by the corona discharge needle of the interface, which applies a large voltage to the nebulized solvent/analyte mixture. The ions (i.e. Oxo-PIP precursor ions) pass through the orifice of the instrument and enter the first quadrupole. Quadrupoles 1 and 3 (Q1 and Q3) are mass filters, allowing selection of ions (i.e., "precursor" and "fragment" ions) based on their m/z. Quadrupole 2 (Q2) is the collision cell, where ions are fragmented. Q1 selects for ions with m/z of precursor ions. Selected precursor ions are allowed to pass into the collision chamber (Q2), while ions with any other m/z collide with the sides of Q1 and are eliminated. Precursor ions entering Q2 may be fragmented with collision activated dissociation (CAD) through collisions with neutral argon gas molecules. Alternatively, if the precursor ions entering Q2 are multiply charged cations, they may be fragmented with electron transfer dissociation (ETD). The fragment ions generated are passed into Q3, where selected fragment ions are collected while other ions are eliminated.

One of ordinary skill is capable of identifying one or more fragment ions of a particular Oxo-PIP precursor ion that may be used for selection in Q3. A specific fragment ion is one that will not be formed in significant amounts by other molecules with similar molecular structures. In contrast, a non-specific fragment ion is one that is formed by molecules other than the desired analyte. Suitable specific fragment ions can be identified by testing various molecular standards to determine whether fragment ions formed by Oxo-PIP are also formed by other molecules with similar structures or features. Preferably, at least one fragment ion specific for Oxo-PIP ions are identified. More preferably, one or more of these fragment ions have m/z of 144+−0.5 or 98+−0.5.

As ions collide with the detector, they produce a pulse of electrons that are converted to a digital signal. The acquired data is relayed to a computer, which plots ion counts per unit time. The areas under the peaks corresponding to particular ions, or the amplitude of such peaks, are measured and the area or amplitude is correlated to the amount of the analyte of interest. The area under the curves, or amplitude of the peaks, for fragment ion(s) and/or precursor ions are measured to determine the amount of Oxo-PIP. As described above, the relative abundance of a given ion may be converted into an absolute amount of the original analyte using calibration standard curves based on peaks of one or more ions of an internal molecular standard. The absolute amount of an analyte detected by LC- or GC-MS/MS can then be converted into an absolute amount of Oxo-PIP that was present in the original test sample.

As explained above, the inventors have also discovered that 6-oxopiperidine-2-carboxylic acid (Oxo-PIP) is a diagnostic biomarker of PDE in a patient. Therefore, this disclosure provides methods of diagnosing a patient that is at risk or is suspected of having PDE by analyzing a biological fluid sample from the patient for the presence of Oxo-PIP in the sample and diagnosing PDE in the patient when Oxo-PIP is detected. Any suitable methods of detecting Oxo-PIP may be used in these methods. In particular, the detection method may include introducing an internal standard into the sample received from a patient and analyzing the sample containing the internal standard using liquid chromatography tandem mass spectrometer (LC-MS-MS) to determine the Oxo-PIP concentration present in the sample. These methods may include adding one or more alcohol(s) and/or organic solvent(s) to the sample and mixing and centrifuging the sample to extract any Oxo-PIP present into the supernatant and then analyzing the supernatant by LC-MS-MS. In these methods, the transitions for Oxo-PIP in mass spectra with the anadem mass spectrometer are at 144.2 to 98.1. In these methods, the liquid chromatography tandem mass spectrometer (LC-MS-MS) may comprise electrospray ionization (ESI) MS. In these methods, the internal standard may be a deuterated internal standard, for example, deuterated Oxo-PIP ($D_3$-Oxo-PIP).

Suitable patient samples that may be analyzed in these methods include biological fluid samples selected from saliva, sweat, urine, blood, serum, plasma, cerebrospinal fluid (CSF), and combinations thereof.

Patients with PDE may be treated with therapeutic intravenous doses of Vitamin B6 and remission from seizures can be maintained through daily doses of Vitamin B6. Therapeutic doses may be 50-100 mg/day, or 15-30 mg/kg/day.

Unfortunately, despite remission of seizure activity with vitamin B6 supplementation, intellectual disability is still frequently seen in patients with PDE. Because the cerebral lysine degradation pathway is limited, dietary lysine restriction is an additional treatment that has demonstrated potential for in addition to pyridoxine supplementation. Lysine restriction of 70-100 mg/kg/day in children less than 1 year of age, or 45-80 mg/kg/day in children between 1-7 years of age, and 20-45 mg/kg/day in children older than 7 years of age has been proposed as target restriction limits in these patients.

This disclosure also provides methods of treating PDE in patients diagnosed with PDE by the detection of the Oxo-PIP in a patient sample. In these methods, a sample from a human patient is analyzed for the presence of Oxo-PIP in the sample. As explained above, the patient is diagnosed with PDE when the presence of Oxo-PIP in the plasma sample is detected. The patient diagnosed with PCE may then be treated by administering an effective amount of vitamin B6 to the diagnosed patient. Alternatively or additionally, the patient may be treated by imposing a lysine-restricted diet on the patient. Alternatively or additionally, the patient may be treated by the administration of pyridoxine supplementation.

The progression and/or treatment of PDE may be measured by analyzing plasma and cerebrospinal fluid levels of Oxo-PIP in patients with PDE. Improvements (i.e., reduction or elimination of detectable Oxo-PIP) may be seen with the implementation of a lysine-restricted diet and/or pyridoxine supplementation and/or Vitamin B6 administration.

Thus, this is disclosure also provides methods of monitoring the presence or progression of PDE in a patient by obtaining a sample from a human patient and detecting the concentration of Oxo-PIP in the sample. A therapeutic change to a PDE treatment is administered to the patient if the concentration of Oxo-PIP is detected in the sample is greater than 100 μmol/mg creatinine. In these methods, the therapeutic change administered to the patient may comprise an administration of Vitamin B6. Alternatively or additionally, the therapeutic change administered to the patient may comprise administration or imposition of dietary restrictions of lysine in the patient's diet.

This disclosure also provides a kit for detecting Oxo-PIP in a sample. These kits may comprise compositions useful for detection and quantitation of Oxo-PIP in a biological sample, such as a deuterated internal standard, for example, $D_3$-Oxo-PIP. The deuterated internal standard may be provided suspended in an aqueous solution or frozen, for instance, in specified concentrations to aid in formation of a standard curve for quantitation of Oxo-PIP in patient samples. The deuterated internal standard may also be provided suspended in a mobile phase for direct spiking into a sample for liquid chromatography.

These kits also may include reagents used to carry out liquid or gas chromatography and tandem mass spectrometry analysis on patient samples, as well as reference and/or instruction materials for conducting such analysis. These reference materials may contain standard curves as well as Oxo-PIP values associated with amounts of Oxo-PIP in a sample that are indicative of a positive or negative diagnosis of PDE in a patient. These kits may further comprise instructions including directions for obtaining a sample, processing the sample, preparing internal standards, and the like. In a preferred embodiment, these kits are provided for use in a method according to the present disclosure.

The following examples serve to illustrate the invention. These examples are in no way intended to limit the scope of the methods.

EXAMPLES

The following chemicals, reagents, and instrumentation were used in conducting the experiments described in the following examples.

Deuterium oxide ($D_2O$), deuterated sulfuric acid ($D_2SO_4$), deuterated chloride (DCl aq), deuterated acetic acid ($CH_3CO_2D$), deuterated ethanol ($CH_3CH_2$-OD), deuterated ammonium hydroxide ($ND_4OD$), L-allysine ethylene acetal (AEA), L-lysine, L-glutamine, a-aminoadipic acid (AAA), pipecolic acid (PIP), L-amino acid oxidase from *Crotalus adamanteus* (Type IV), Lysine Oxidase from *Trichoderma viride*, Catalase from bovine liver, L-saccharopine, nicotinamide adenine dinucleotide ($NAD^+$), 2,4-dinitrophenyl hydrazine (DNPH), uridine 5'-diphosphoglucuronic acid (UDPGA) trisodium salt, and amberlyst-15 were purchased from Sigma-Aldrich Chemical Company (St. Louis, MO). D3-a-Aminoadipic acid (d3-DL-α-AAA) was acquired from CDN Isotopes (Quebec, Canada), and all other reagents were procured from Fisher Scientific (Pittsburgh, PA). Control human plasma ($K_2EDTA$), blood, and urine were purchased from Bioreclamation, LLC (Westbury, NY). Human liver cytosol, S9 and microsomal subcellular fractions were procured from Xenotech, LLC (Kansas City, KS). The $^1H$ and $^{13}C$ NMR spectra were recorded using a 400 MHz Bruker NMR, Avance III 400; the $^1H$-NMR spectra were collected at 400 MHz while the $^{13}C$-NMR spectra were collected at 100 MHz and the chemical shifts are reported in ppm. An Applied Biosystems Sciex 4000 (Applied Biosystems; Foster City, CA) equipped with a Shimadzu HPLC (Shimadzu Scientific Instruments, Inc.; Columbia, MD) and a Leap auto-sampler (LEAP Technologies; Carrboro, NC) was used to analyse metabolites.

Human subjects were recruited via the Inherited Metabolic Disease Clinic at the Children's Hospital of Colorado on an IRB-approved study. Inclusion criteria included PDE due to α-AASA dehydrogenase deficiency documented by the presence of bi-allelic mutations in ALDH7A1 and elevation of α-AASA/$Δ^1$-P6C in body fluids on clinical laboratory testing. From these subjects, blood, plasma, urine, and CSF samples were obtained. A control group included anonymous samples obtained during the same period of discarded plasma originally obtained for clinical testing at the clinical chemistry laboratory at the Children's Hospital of Colorado under an IRB-approved protocol.

Liquid chromatography tandem mass spectrometry experiments: Lysine metabolites were first analyzed based on previously published liquid chromatography tandem mass spectrometry (LC-MS/MS) methods (Struys, Jakobs 2007, Molecular Genetics and Metabolism 91:405; Yuzyuk et al. 2016, J Chromatogr B Analyt Technol Biomed Life Sci, 1017-1018:145-52). As the goal of this study was to replicate current newborn screening modalities, we focused on a non-derivatized MS/MS analytical method (Nagy et al. 2003, Rapid Commun Mass Spectrom 17:983-90). Samples were analyzed via electrospray ionization in positive ion mode (ESI+) using an Applied Biosystems Sciex 4000 (Applied Biosystems) equipped with a Shimadzu HPLC (Shimadzu Scientific Instruments) and a Leap auto-sampler (LEAP Technologies). Methanol (MeOH):acetonitrile (ACN) 200 µL 1:1 mixture was added to 100 µL of plasma, blood, urine, CSF or standard materials. Plasma and blood samples were centrifuged at 10,000 rpm and the supernatants used. Urine and CSF samples required no additional processing. The liquid chromatography separation of 10 µL sample was done on two tandem Zorbax-C8 150×4.6 mm 5 micron columns with a Zorbax-C8 guard column (Agilent Technologies) operated at 40° C. with a 0.4 mL/min flow-rate, using the mobile phases A (10 mM NH4OAc, 0.1% formic acid in H2O) for 12.0 mM, linear ramp to 95% mobile phase B (1:1 ACN:MeOH) at 16.0 min, held for 11.5 min, followed by ramping back to A and held for a total run time of 32.0 min. Samples were analyzed using the following conditions: i) ion-spray voltage of 5500 V; ii) temperature, 450° C.; iii) collision using nitrogen gas with curtain gas (CUR) set at 10 and collisionally activated dissociation (CAD) set at 12; iv) ion source gas one (GS1) and two (GS2) were set at 30; v) entrance potential was set at 10 V; vi) quadruple one (Q1) and (Q3) were set on unit resolution; vii) dwell time was set at 200 msec. The retention times, mass transitions and other settings are listed in Table 1.

TABLE 1

Liquid chromatography-tandem mass spectrometry method

| Metabolite | tR (min) | Mass transition m/z | DP | CE | CXP |
|---|---|---|---|---|---|
| Lysine | 7.2 | 147.2 → 130.0 | 41 | 15 | 8 |
| | | 147.2 → 84.0 | 41 | 23 | 4 |
| L-glutamine | 7.6 | 147.2 → 130.0 | 41 | 15 | 8 |
| | | 147.2 → 84.0 | 41 | 23 | 4 |
| 2-amino-adipic acid | 8.2 | 162.2 → 98.4 | 41 | 23 | 8 |
| $Δ^2$-piperideine-6-carboxylate | 8.5 | 128.2 → 82.1 | 66 | 19 | 4 |
| | | 128.2 → 55.1 | 66 | 31 | 10 |
| | | 255.3 → 211.1 | 46 | 13 | 14 |
| $Δ^1$-piperideine-6-carboxylate | 9.0 | 146.3 → 128.0 | 31 | 13 | 8 |
| | | 146.3 → 82.2 | 31 | 23 | 4 |
| 6-hydroxy-pipecolate | | 128.2 → 82.1 | 66 | 19 | 4 |
| | | 128.2 → 55.1 | 66 | 31 | 10 |
| Pipecolic acid | 9.2 | 130.3 → 84.1 | 41 | 23 | 4 |
| $Δ^1$-piperideine-2-carboxylic | 10.3 | 128.2 → 82.1 | 66 | 19 | 4 |

TABLE 1-continued

Liquid chromatography-tandem mass spectrometry method

| Metabolite | tR (min) | Mass transition m/z | DP | CE | CXP |
|---|---|---|---|---|---|
| Piperidine-2-hydroxy-2-carboxylate | 11.2 | 146.3 → 128.0 | 31 | 13 | 8 |
|  |  | 128.2 → 82.1 | 66 | 19 | 4 |
| L-allysine ethylene acetal | 12.3 | 190.2 → 128.0 | 31 | 15 | 8 |
|  |  | 128.2 → 82.1 | 66 | 19 | 4 |
| 6-oxo-pipecolate | 13.7 | 144.2 → 98.1 | 41 | 19 | 6 |
|  | 15.9 | 144.2 → 98.1 | 41 | 19 | 6 |

DP, delustering potential;
CE, collision energy;
CXP, collision cell exit potential Formation and Characterization of $\Delta^1$-P6C, α-AASA and 6-hydroxypiperidine-2-carboxylic Acid (P6CH) from L-allysine Ethylene Acetal (AEA)

Amberlyst-15 method: AEA (11.4 mg) was dissolved in $H_2O$ (1.0 ml) with 76 mg Amberlyst-15 and stirred for 30 min at RT. After settling, the liquid was transferred to a new glass vial, the beads were then washed with $NH_4OH$ (2×1.0 mL), and the contents combined; in some experiments the material was then concentrated under a $N_2$ stream and reconstituted with water to a final concentration of 30 mM. For the deuterated experiment, AEA (71 mg) was dissolved in $D_2O$ (2.0 mL) and Amberlyst-15 (721 mg) added and stirred at RT (6 hr) at which point the $D_2O$ was removed and $ND_4OD$ (1.0 mL) added, stirred (15 min), the solution was removed, and NMR spectra collected.

Acid catalyzed method: AEA 11.6 mg was dissolved in 1.0 mL $H_2O$ followed by addition of 50 μL concentrated HCl or $H_2SO_4$ and stirred for 30 min. Thereafter, the solution was diluted with 2 mL water to a concentration of 20 mM. Additional experiments were performed where 5.0 mg of AEA was diluted with $H_2O$ (1.3 mL) and then various amounts of HC 1 (20 or 50 μL) were added and samples analysed by LC/MS-MS.

NMR experiments: AEA (10 mg) was dissolved in 700 μL $D_2O$ followed by addition of either 50 μl DCl or $D_2SO_4$, and immediately transferred to a NMR tube and $^1H$ and/or $^{13}C$ spectra collected using a 400 MHz Bruker NMR; the 1H-NMR spectra were collected at 400 MHz while the 13C-NMR spectra were collected at 100 MHz and the chemical shifts are reported in ppm. Additional NMR experiments were performed; P6C/P6CH was prepared via $D_2O$ via DCl conditions followed by the addition of $NaHCO_3$ (1.5 equivalents) to produce Δ2-P6C.

Aldehyde detection via 2,4-dinitrophenyl hydrazine (DNPH) experiment and infrared spectroscopy: The 2,4-DNP reagent procedure was prepared as previously described with minor modifications (Ruekberg, Rossoni 2005, J. Chem. Educ. 82:1310). 500 mg of 2,4-DNP was weighed out into a 25 ml Erlenmeyer flask and 4.0 ml water and 11.0 ml ethanol were added and stirred while 2.5 ml H2SO4 was added dropwise. The exothermic reaction was cooled with an ice bath. The contents were then allowed to warm to room temperature and stirred until completely into solution. 200 μL of this solution was added to the analyte solution either during or after the generation from AEA.

A sample of 2,4-DNP reagent was added to a stock solution of the material prepared from AEA for the 2,4-DNP reactivity test. In addition, a lyophilized sample of P6C/P6CH material produced from AEA HCl conditions produced a sticky oil to probe aldehyde characteristics via IR spectrum.

Enzymatic production of lysine metabolism products: To evaluate the products of lysine metabolism through the pipecolate pathway we synthesized the intermediate $\Delta^1$-P2C enzymatically as follows. Lysine 50 mM with 100 μL bovine catalase (12.1 mg catalase powder in 1.0 mL PBS buffer pH 7.4) and 50 μL *T. viridae* lysine oxidase (acquired enzyme diluted with 250 μL water) in 750 μL PBS were incubated at 37° C. for 1 hr, and 100 μL samples were obtained at 0.5, 2, 5, 10, 15, 30, 45 and 60 min, added to 300 μL MeOH:ACN, and analyzed via LC-MS/MS. To identify the reaction product of the saccharopine pathways, recombinant saccharopine dehydrogenase domain of human AASS-SDH was expressed in insect Sf9 cells and purified by chromatography methods. Stock saccharopine (10 mM; 100 μL; 1.0 mM final) and NAD+ (100 μL; 1.0 mM final) were added to PBS (790 μL; pH 7.4), and after preincubation at 37° C. for 5 min, the reaction was initiated by addition of 10 μL purified human AASS-SDH and 100 μL samples taken at 0.5 min, 5, 10 and 15 min, were diluted with 400 μL 1:1 MeOH:ACN and analyzed by LC-MS/MS. α-AASA dehydrogenase was expressed in BL21 Star™ (DE3) *E. coli* (ThermoFisher) cultures transformed with the pET15b vector containing ALDH7A1, and harvested 3 hr after induction by 1.0 mM JPTG. Expression culture lysate was combined with 2.2 mM NAD+ and 0.6 mM $\Delta^1$-P6C for 5 min at 30° C. and quenched by adding 100 μL glacial acetic acid to reaction solution (500 μL).

Cytosolic and mitochondrial metabolism of lysine metabolites: Human liver cytosol 100 μL (10 mg/mL) or S9 fraction 100 μL (20 mg/mL) and 100 μL NAD+ (1.2 mM final) in 400 μL PBS pH 7.4 were preincubated at 37° C. for 5 min, followed by addition of 100 μL Δ1-P6C (100 μM); 100 μL samples were taken at 0.5, 5, 20 and 50 min, added to 300 μL 1:1 MeOH:ACN and analysed by LC-MS/MS. To probe potential phase II metabolism, 100 μL human liver microsomes (20 mg protein/mL) were similarly incubated with 4.0 mM UDPGA.

Human liver mitochondria were freshly prepared by homogenization of a human liver sample with a Teflon pestle in 5% weight to volume Zheng buffer (Zheng et al. 1990, Biochim Biophys Acta 1019:1-10), and after centrifugation at 5600 g for 5 min, the supernatant was transferred to a centrifuge tube; this procedure was repeated on the resuspended pellet a second time. Both supernatants were combined, centrifuged at 37,500 g for 5 min, the resulting pellet resuspended in Zheng buffer, homogenized and similarly pelleted again, and resuspended in 300 μL Zheng buffer to provide a mitochondrial preparation, with protein concentration determined using the Bio-Rad Protein Assay. To access the mitochondrial matrix, the homogenate was subjected to 3 freeze-thaw cycles, followed by 2×7 bursts of sonication on ice using a Branson 450 digital sonifier with a 2-inch cup horn at 30% amplitude. Of this mitochondrial preparation 100 μL was similarly incubated with Δ1-P6C and analyzed as above.

Reaction products of AASS enzyme via saccharopine dehydrogenase and are substrate of AASA-dehydrogenase. To confirm the conversion of saccharopine to P6CH/$\Delta^1$-P6C, we utilized the saccharopine dehydrogenase (SDH) activity associated with α-aminoadipic semialdehyde synthase (AASS). To PBS (790 μL; pH 7.4) was added 10 mM stock solution saccharopine (100 μL 1.0 mM final) and NAD+ (100 μL; 1.0 μL final), and the mixture was preincubated at 37° C. for 5 min, and the reaction initiated by the addition of 10 μL purified human AASS. Samples (100 μL) were taken at 0.5 min, 5, 10, and 15 min and placed into 1:1 MeOH:ACN (400 μL), mixed, centrifuged, and the supernatants analyzed by LC/MS-MS. BL21 Star™ (DE3) *E. coli* (ThermoFisher) cultures that had been transformed with the pET15b vector containing ALDH7A1 were used to express AASA-dehydrogenase. Cells were harvested 3 hr after induction by 1.0 mM IPTG, snap frozen in liquid nitrogen and stored at −80° C. Expression culture lysate was combined with NAD$^+$ (2.2 Mm) and P6C/P6CH (0.6 Mm) for 5 min at 30° C. Following a 1:5 addition of glacial acetic acid, the reaction products were analyzed by LC-MS/MS.

Synthesis of internal standard D3-Oxo-PIP: DL-2-Amino-1,6-hexanedioic-2,5,5-d$_3$ Acid (D$_3$-AAA; 40 mg, 0.24 mmol) was refluxed in 20% mono-deuteroacetic acid (CH$_3$COOD)/D$_2$O (1.0 mL) at 108° C. for 3.5 h. The solvent was evaporated under reduced pressure and contents dried on high vacuum (1.0 hr). Deuterated ethanol (CH$_3$CH$_2$OD; 10 mL) was added to the reaction mixture, stirred, and filtered through filter paper. To the solid filtrate was added additional CH$_3$CH$_2$OD (10 mL), mixed and filtered a 2$^{nd}$ time through filter paper. The two filtrate solutions were combined and concentrated on reduced pressure and dried on high vacuum (4 hr); deuterated Oxo-PIP (14 mg) was obtained and >97% pure as shown by NMR and LC/MS-MS analysis.

Biomarker stability studies: In a 4-month stability study, fresh urine samples (400 μL) from two subjects were aliquoted into 1.5 mL Eppendorf tubes and stored either at room temperature (22±2° C.), freezer (−13±3° C.) or deep freezer (−77±3° C.) and sampled over four-months.

Computational calculations: Chemical structures were drawn using ChemDraw Ultra 6.0.1 and z-matrix utilized to perform calculations via Gaussian G98w. Structures were optimized using molecular mechanics and calculations performed at the HF/6-31G level of theory, followed by B3LYP//HF/6-311++G. Computational energy values are summarized in Table 2.

TABLE 2

Computational Energy Summary

| Compound | HF/ 6-31G | Hartree Energies B3LYP - HF/ 6 - 311++G | 1 Hartree (kcal/mol) 627.51 |
|---|---|---|---|
| Pipecolic acid | −437.600 | −440.456 | −276390.306 |
| Δ$^1$-piperideine-2-carboxylate | −436.429 | −439.240 | −275627.805 |
| Piperidime-2-hydroxy-2-carboxylate | −512.431 | −515.677 | −323592.492 |
| Δ$^1$-piperideine-6-carboxylate | −436.423 | −439.236 | −275624.829 |
| 6-hydroxy-pipecolate-Cis | −512.439 | −515.682 | −323595.797 |
| 6-hydroxy-pipecolate-Trans | −512.428 | −515.677 | −323592.528 |
| Lysine | −493.770 | −497.014 | −311881.433 |
| Lysine-6-imine | −492.587 | −495.787 | −311111.608 |
| Lysine-2-imine | −492.584 | −495.787 | −311111.172 |
| 2-aminoadipic acid | −587.263 | −590.907 | −370800.074 |

TABLE 2-continued

Computational Energy Summary

| Compound | HF/ 6-31G | Hartree Energies B3LYP - HF/ 6 - 311++G | 1 Hartree (kcal/mol) 627.51 |
|---|---|---|---|
| α-aminoadipic semialdehyde-Hydrate | −588.422 | −592.107 | −371553.149 |
| α-aminoadipic semialdehyde | −512.418 | −515.668 | −323586.677 |
| 6-oxo-pipecolate | −511.278 | −514.485 | −322844.396 |
| 6-oxo-pipecolate-Enol | −511.255 | −514.463 | −322830.872 |
| Glutamate | −548.246 | −551.596 | −346132.009 |
| 2-oxoglutarate | −566.887 | −570.244 | −357834.046 |
| Saccharopine | −985.858 | −992.063 | −622529.634 |
| Saccharopine-Imine-Trans | −984.674 | −990.838 | −621760.707 |
| Saccharopine-Imine-Cis | −984.665 | 990.828 | 621754.438 |
| Hydrogen peroxide | −150.710 | −151.553 | −95100.796 |
| Hydrogen | −1.127 | −1.177 | −738.293 |
| Water | −75.985 | −76.426 | −47957.888 |
| Ammonia | −56.166 | −56.559 | −35491.050 |
| Oxygen | −149.462 | −150.260 | −94289.840 |

Example 1

Preparation of a-aminoadipic Semialdehyde (α-AASA) and Δ$^1$-piperideine-6-carboxylate (Δ$^1$-P6C We aimed to develop an LC/MS-MS method to monitor α-AASA and Δ$^1$-P6C, but without the commonly used derivatization methods. We developed an LC/MS-MS method which detected allysine ethylene acetal (AEA) at a t$_R$=12.3 min using the transition MRM of 190.2→128.0 m/z. We then prepared a purposed α-AASA/Δ$^1$-P6C mixture using the Amberlyst-15/NH$_4$OH method described above, similar to previously described methods. Analyzing the α-AASA and Δ$^1$-P6C mixture products as non-derivatized samples via electrospray ionization in positive ion mode (ESI+), we observed the expected M+H$^+$ ions: α-AASA 146 m, and Δ$^1$-P6C 128 m/z and their described daughter ions: α-AASA transitions 146.3 4→128.0, 82.1 and 55.1 m/z ions; Δ$^1$-P6C transitions 128.2→82.0, and 55.0 m/z. The LC/MS-MS method resolved both components with Δ$^1$-P6C at t$_R$=8.5 min and α-AASA at t$_R$=9.0 min. As summarized in Table 2, we found that the observed ratio of t$_R$=8.5 min presumed Δ$^1$-P6C and t$_R$=9.0 min presumed α-AASA depended on the sample preparation such as the catalyst (i.e. use of H$_2$SO$_4$ or HCl versus Amberlyst-15), time, and the pH of the solution. For example, if the acetal was deprotected via acid-catalyzed conditions without pH neutralization, we only observed the signal at t$_R$ 9.0 min corresponding to α-AASA (FIG. 6), enabling further characterization through DNPH reactivity and NMR spectroscopy. We concluded that the observed 8.5 min/9.0 min peak ratio (Δ$^1$-P6C and α-AASA) was a function of the conditions, time and pH adjustment used to deprotect the acetal.

TABLE 3

Conditions used to produce Δ$^2$-P6C, Δ$^1$P6C, 6-OH-PIP mixtures

| mg AEA | ml H2O | Conditions | Time | 8.5 min % Δ$^2$-P6C | 9.0 min % Δ$^1$-P6C | 9.0 min %6-OH-PIP | 12.3 min % AEA |
|---|---|---|---|---|---|---|---|
| 5.0 | 1.3 | HCl (20 microL) | 3 min | 0 | 10 | 2 | 88 |
| 5.0 | 1.3 | HCl (20 microL) | 30 min | 0 | 49 | 21 | 30 |
| 5.0 | 1.3 | HCl (20 microL) | 60 min | 0 | 57 | 25 | 18 |
| 5.0 | 1.3 | HCl (20 microL) | 90 min | 0 | 63 | 29 | 8 |
| 5.0 | 1.3 | HCl (20 microL) | 150 min | 0 | 67 | 32 | 1 |

TABLE 3-continued

Conditions used to produce $\Delta^2$-P6C, $\Delta^1$P6C, 6-OH-PIP mixtures

| mg AEA | ml H2O | Conditions | Time | 8.5 min % $\Delta^2$-P6C | 9.0 min % $\Delta^1$-P6C | 9.0 min %6-OH-PIP | 12.3 min % AEA |
|---|---|---|---|---|---|---|---|
| 5.0 | 1.3 | HCl (20 microL) | 150 min | 0 | 67 | 32 | 1 |
| 5.0 | 1.3 | HCl (20 microL) | 1.5 days | 3 | 65 | 32 | 0 |
| 5.0 | 1.3 | HCl (20 microL), pH adjusted to 9 | 30 min | 12 | 59 | 29 | 0 |
| 5.0 | 1.3 | HCl (50 microL) | 3 min | 0 | 29 | 14 | 57 |
| 5.0 | 1.3 | HCl (50 microL) | 30 min | 0 | 69 | 31 | 0 |
| 5.0 | 1.3 | HCl (50 microL) | 2.0 days | 4 | 66 | 30 | 0 |
| 5.0 | 1.3 | HCl (50 microL), pH adjusted to 9 | 4 hours | 13 | 58 | 29 | 0 |
| 5.0 | 1.3 | H2SO4 (50 microL) | 3 min | 0 | 26 | 12 | 62 |
| 5.0 | 1.3 | H2SO4 (50 microL) | 30 min | 0 | 68 | 32 | 0 |
| 5.0 | 1.0 | Amberlyst-15/NH4OH (2 mL) | 1.0 hr | 32 | 44 | 24 | 0 |
| 5.0 | 1.0 | Amberlyst-15/NH4OH (2 mL), nH 7.0 | 1.0 hr | 12 | 57 | 31 | 0 |

$\Delta^2$-P6C, $\Delta^2$-piperideine-6-carboxylate;
$\Delta^1$-P6C, $\Delta^1$-piperideine-6-carboxylate;
6-OH-PIP, 6-hydroxy-pipecolate Aldehyde detection via 2,4-dinitrophenyl hydrazine: 2,4-DNP reagent was added to positive controls including 4-ethoxybenzaldehyde (3.4 mg; red precipitant), octanal (4.2 mg; yellow precipitant), hexanal (3.8 mg; yellow precipitant) and acetone (5.6 mg; yellow precipitant). Compounds were prepared in 1.5 mL Eppendorf tubes as 50% ethanol solutions (400 µL) and 2,4-DNP reagent (200 µL) was added and mixed. Two different AEA 2,4-DNP reactions were performed with AEA. First, AEA (5.0 mg) was diluted with water (150 µL) and 50% ethanol (150 µL). 200 µL of the 2,4-DNP reagent (containing sulfuric acid) was immediately added and a chemical reaction was noted with formation of a yellow precipitant, which was characterized by LC-MS/MS to have a mass consistent with 2,4-DNP-AASA adduct (FIG. S2A). Next, we allowed the AEA reaction to occur for 1.0 hr followed by 50% ethanol (150 µL). Once this reaction was completed, 200 µL of the 2,4-DNP reagent was added without evidence of a chemical reaction. The reaction was warmed at 37° C. and allowed to cool without evidence of solid formation (chemical reaction). This data suggested that the aldehyde, which is present during formation, rapidly cyclized and is no longer present in the final product. To verify this assumption, NMR spectroscopy was performed.

Example 2

P6CH/$\Delta^1$-P6C not α-AASA/$\Delta^1$-P6C

Figure 2:
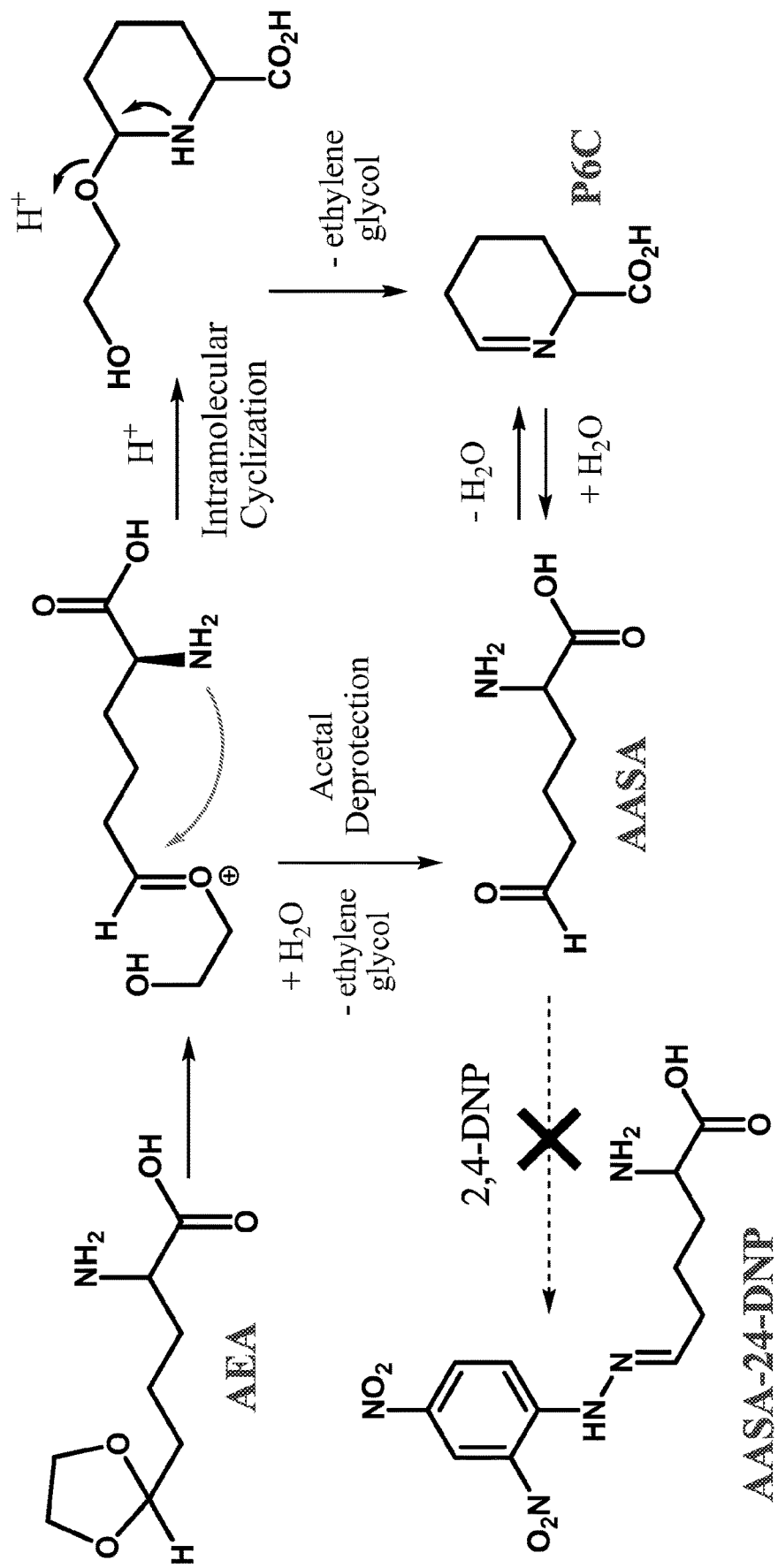
FIG. 2: AEA conversion to AASA and $\Delta^1$-P6C.

Given the reported poor stability of α-AASA and $\Delta^1$-P6C in biological samples, we intended to derivatized the aldehyde within α-AASA with 2,4-dinitrophenyl hydrazine (2,4-DNP; FIG. 2) to a more stable compound with a potentially better LC/MS-MS sensitivity. Surprisingly, we observed no reaction when mixing a fresh batch of α-AASA and $\Delta^1$-P6C prepared by the Amberlyst 15/NH4OH method with 2,4-DNP reagent. An infrared spectrum of lyophilized α-AASA/$\Delta^1$-P6C mixture did not show a characteristic aldehyde transition at 2700 cm$^{-1}$. These experimental results were not in agreement with the notion that aldehyde α-AASA was produced from AEA.

Figure 3:
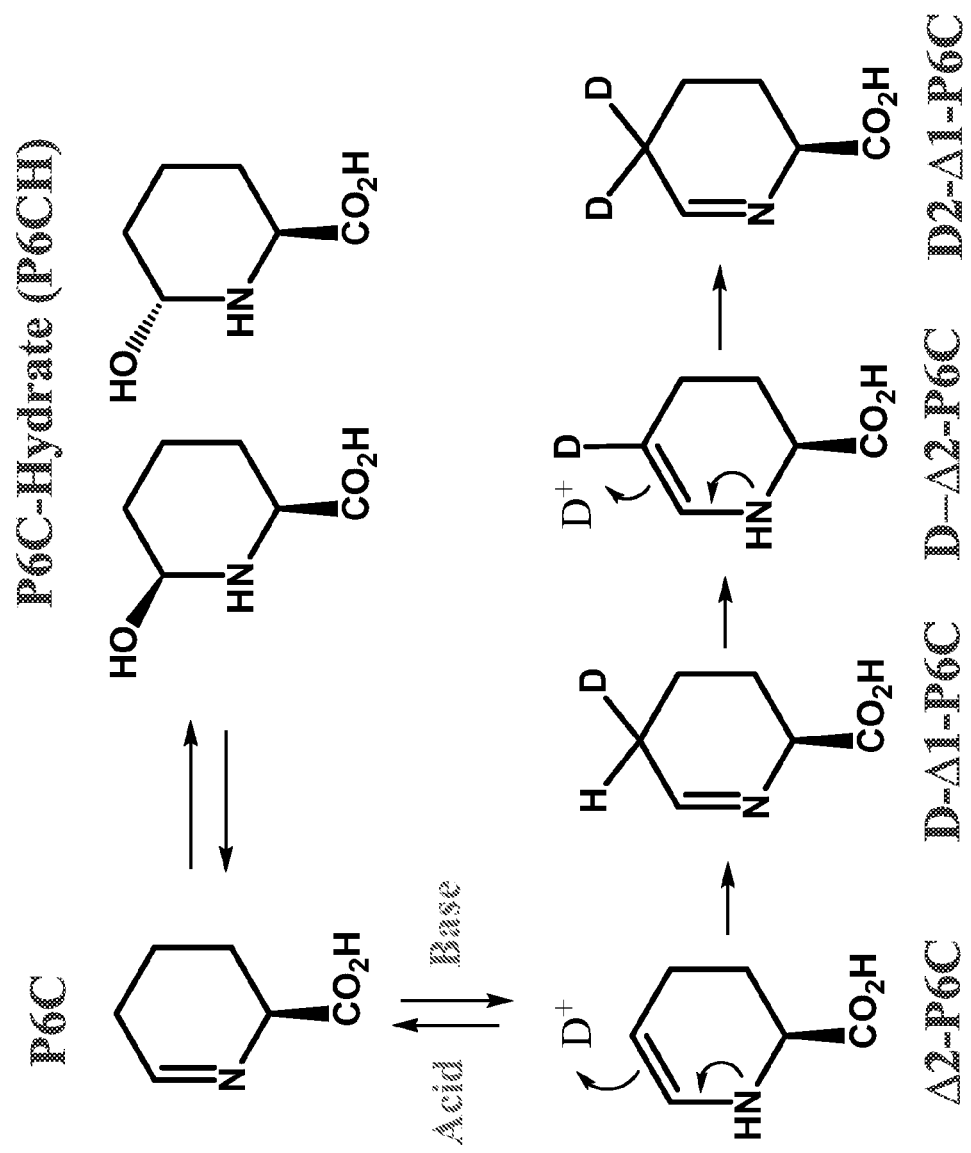
FIG. 3: Proposed $\Delta^2$-P6C/$\Delta^1$-P6C/P6CH equilibrium.

To reconcile the discrepancy between our findings and previously published assumptions, we performed a series of $^1$H and $^{13}$C NMR experiments. Both $^1$H and $^{13}$C-NMR of AEA confirmed the starting material and relative purity. To study its products, we dissolved AEA in D$_2$O and added either DCl or D$_2$SO$_4$ to initiate the reaction and collected the $^1$H-NMR and $^{13}$C-NMR spectra. Consistent with not forming an aldehyde, we did not observe a $^1$H-NMR aldehyde—CH signal around 9-11 ppm, however, we did observe a downfield signal at 8.2 ppm. The $^1$H-NMR for DL-$\Delta$1-pyrroline-5-carboxylic acid exhibits an alkene—CH signal around 7.7 ppm, and thus we interpret the 8.2 ppm signal in our collected spectrum to correspond to the—CH alkene within $\Delta^1$-P6C, similar to the alkene—CH signal at 7.7 ppm published for DL-$\Delta^1$-pyrroline-5-carboxylic acid (Farrant et al. 2001, J Biol Chem 276:15107-116). In addition to $\Delta^1$-P6C, the $^1$H-NMR data was also more consistent with the cyclic form of α-AASA, 6-hydroxypiperidine-2-carboxylic acid (P6CH), which corresponds to the hydrated form of $\Delta^1$-P6C (P6CH; FIG. 3). In addition, the $^{13}$C-NMR signals at 80.5 and 80.7 ppm are consistent with the secondary alcohol carbons within 6-hydroxy-pipecolate (piperidine-6-hydroxy-2-carboxylate, 6-OH-PIP) with the 146 parent mass. Thus, the 1H-NMR data, 13C-NMR and LC-MS/MS data suggest a mixture of compounds, which co-elutes at $t_R$ 9.0 min with an apparent 1:2 ratio via LC-MS/MS with respective m/z of 128 and 146. Despite a number of experimental conditions including the use of a C18, silica, amine and cyano columns for the LC-MS/MS experiments, we could not separate what we believe is a $\Delta^1$-P6C/6-OH-PIP mixture. Thus, under acidic conditions (HCl, H$_2$SO$_4$), the acetal produces the main signal at $t_R$ 9.0 min, but the NMR data illustrates that it is really a mixture of P6CH/$\Delta^1$-P6C. Therefore, the initial assignment that LC/MS-MS peak at 8.6 min was $\Delta^1$-P6C was not correct. Rather, both P6CH and $\Delta^1$-P6C elute at 9.0 min and their relative LC-MS/MS ratios (1:2) were consistent with the relative amounts observed via $^1$H and $^{13}$C-NMR.

α-AASA and $\Delta^1$-P6C are in equilibrium although this equilibrium is not well understood. Previous studies have noted the difficulty in detecting α-AASA, which is supported by our data and suggests the equilibrium favors $\Delta^1$-P6C. Computational calculations show that the cyclic forms of 6-OH-PIP-Cis and 6-OH-PIP-Trans are energetically more stable than the linear aldehyde α-AASA by 9.1 and 5.9 kcal/mol (Table 2). Intramolecular cyclization of α-AASA without loss of water to $\Delta^1$-P6C/6-OHPIP is an energetically favorable process.

In summary, we concluded that the peak at 8.6 min corresponds to another compound. We assigned this peak to be $\Delta^2$-piperideine-6-carboxylate ($\Delta^2$-P6C). We contend that $\Delta^2$-P6C is in equilibrium (FIG. 3) with $\Delta^1$-P6C, with $\Delta^2$-P6C forming more under neutral to basic conditions, and where $\Delta^2$-P6C can convert back to $\Delta^1$-P6C but with incorporation of deuterium under $D_2O$ with corresponding loss of the proton signal at 1.8 ppm. Additional evidence for $\Delta^2$-P6C comes from conducting two different NMR experiments; first, the Amberlyst-15 experiment but working up with deuterated ammonium hydroxide, and second, conducting deprotection with $DCl/D_2O$ conditions to give P6C/P6CH followed by neutralizing acid and making slightly basic with $NaHCO_3$. There is evidence of the $\Delta^2$-P6C double bond in the $^{13}$C-NMR spectra (108.6 and 127.9 ppm), signals not found when one uses DCl or $D_2SO_4$ conditions. Hence, the α-AASA/$\Delta^1$-P6C equilibrium previously observed and reported appears more appropriately represented in FIG. 3 wherein $\Delta^1$-P6C is in equilibrium with P6CH, not α-AASA, with P6CH forming more under neutral to basic conditions. P6CH can convert back to $\Delta^1$-P6C but with incorporation of deuterium under $D_2O$. Thus, the two peaks of observed reaction products correspond to P6CH at $t_R$ 8.6 min, and a mixture of $\Delta^1$-P6C and 6-OH-PIP at 9.0 min, with the relative amounts a function of the conditions, time, and pH adjustment used to deprotect the acetal. P6CH formation is consistent with a lack of reactivity with 2,4-DNP, as the actual product is not aldehyde α-AASA. P6CH formation can be viewed as the simple addition of water across the C=N bond in $\Delta^1$-P6C to produce P6CH.

Example 3

P6CH/$\Delta^1$-P6C Formed from α-aminoadipic Semialdehyde Synthase

Having demonstrated the chemical generation of standards from AEA produced P6CH/$\Delta^1$-P6C rather than α-AASA/$\Delta^1$-P6C, we next wanted to confirm that the enzyme a-aminoadipic semialdehyde synthase (AASS) in the main enzymatic pathway (the saccharopine pathway) produced the same metabolites. We incubated saccharopine with purified AASS and $NAD^+$, and observed the reaction products $\Delta^1$-P6C/P6CH on LC-MS/MS, and the products formed also failed to give a positive 2,4-DNP test. With this confirmation, we concluded that P6CH, not α-AASA, is the product of AASS and the substrate(s) for the α-AASA dehydrogenase enzyme.

Example 4

(S)-6-oxopiperidine-2-carboxylic acid

Figure 4:
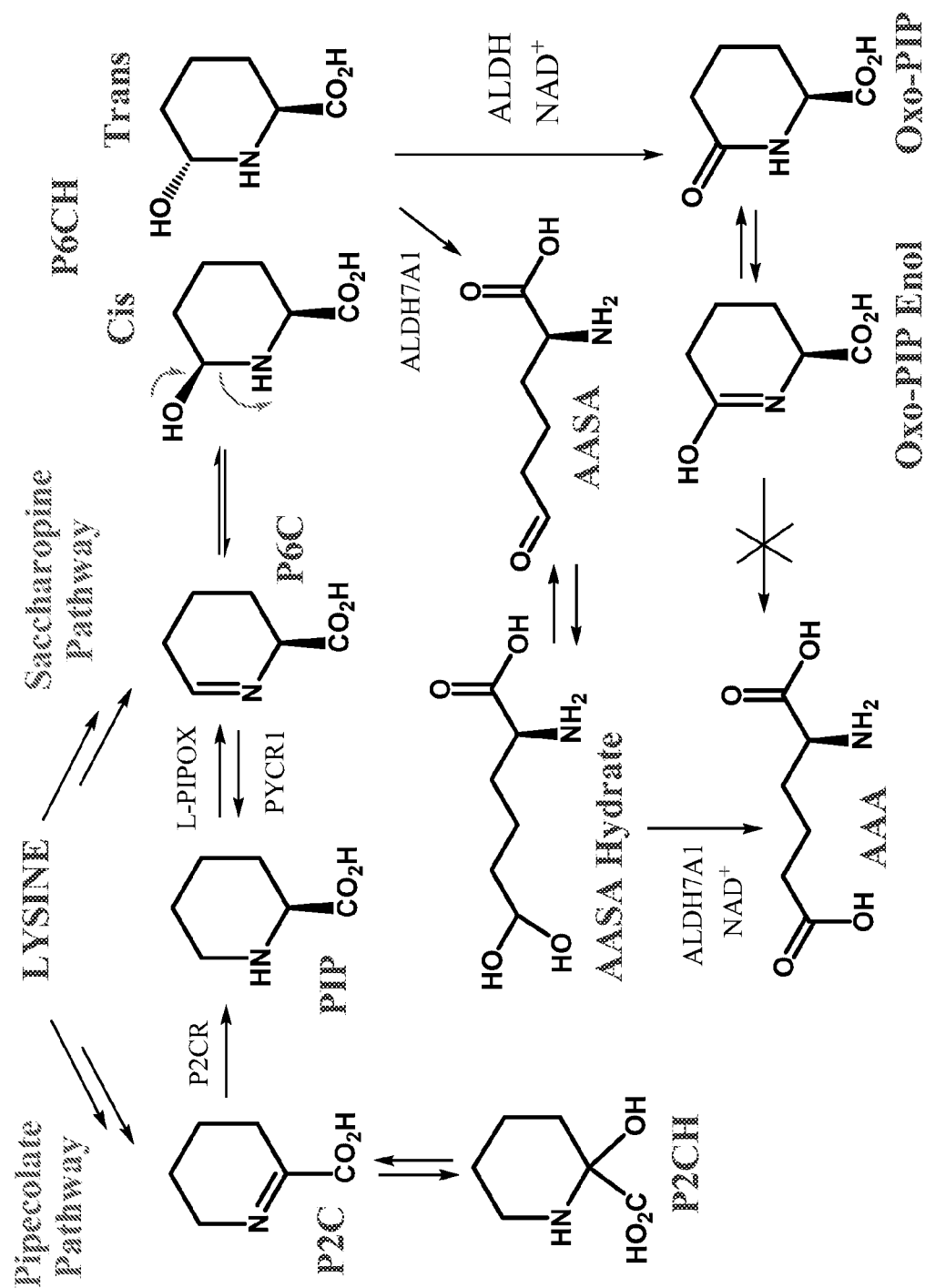
FIG. 4: Proposed modification to the lysine oxidation pathway. Legend: In the revised lysine oxidation pathway both the pipecolate and the saccharopine pathway converge on the equilibrium of $\Delta^1$-piperideine-6-carboxylate ($\Delta^1$-P6C) and 6-hydroxypipecolate (6-OH-PIP). The α-aminoadipic semialdehyde (α-AASA) dehydrogenase enzyme acts on this metabolite to generate α-AASA and then 2-aminoadipic acid (AAA). In α-AASA dehydrogenase deficiency, a cytosolic enzyme catalyzed the oxidation of 6-OH-PIP to 6-oxopipecolate (6-oxo-PIP). Abbreviations: P2C, $\Delta$1-piperideine-2-carboxylate; P2H2C, piperidine-2-hydroxy-2-carboxylate; P2CR, $\Delta$1-piperideine-2-carboxylate reductase; PIP, pipecolic acid.

The next step in the pathway would need to convert P6CH to AAA. The initial ring opening from PC6H to α-AASA prior to oxidation to AAA is an energetically uphill process, and requires an enzyme catalyzed reaction, in this case α-AASA dehydrogenase (FIG. 4). Incubation of purified α-AASA dehydrogenase with the $\Delta^1$-P6C/P6CH mixture without α-AASA readily produced AAA, indicating that this enzyme catalyzes the ring opening and subsequent oxidation of $\Delta^1$-P6C/6OH-PIP.

Given that P6CH has a secondary alcohol, an alternative pathway to AAA could exist by first oxidation of the alcohol of P6CH to (S)-6-oxopiperidine-2-carboxylic acid (6-oxopipecolic acid, 6-oxo-PIP), an amide, followed by hydrolytic ring opening to afford AAA (FIG. 4).

Incubating the $\Delta^1$-P6C/P6CH mixture with a fresh purified mitochondrial preparation only afforded AAA, but incubation of $\Delta^1$-P6C/P6CH with human liver cytosol and with the S9 fraction in the presence of NAD+ showed formation of AAA and small amounts of 6-oxo-PIP. Albeit small, the formation of 6-oxo-PIP raises the possibility of a second pathway. To evaluate if the next step in the hydrolytic ring opening of 6-oxoPIP to afford AAA could proceed, we incubated 6-oxo-PIP with human cytosol, human S9 and human plasma (e.g. esterase activity) incubations, but none of these experiments showed a conversion of 6-oxo-PIP to AAA. Thus, this alternative mechanism to AAA is not a major pathway.

Next, we evaluated if the cytosolic formation of 6-oxo-PIP from P6CH would occur through the α-AASA dehydrogenase enzyme. Incubating purified α-AASA dehydrogenase enzyme with P6CH/$\Delta^1$-P6C resulted in the formation of AAA but did not produce any 6-oxo-PIP in contrast to S9 incubation. Therefore, a different cytosolic alcohol dehydrogenase must be responsible for the oxidation of P6CH to 6-oxo-PIP. We conclude that the enzyme (ALDHs; α-AASA dehydrogenase, Antiquitin) recognizes cyclic P6CH and overcomes the barrier to ring opening to form aldehyde α-AASA, which then becomes oxidized to AAA. Various mutations in ALDH7A1 create a deficiency in either the ring opening process or the alcohol oxidation resulting in accumulation of P6CH. Accumulated P6CH can then be the substrate for this alternative in vivo oxidation pathway resulting in the formation of Oxo-PIP.

Example 5

Monitoring Pathway Metabolites

To complete the LC/MS-MS method, $\Delta^1$-piperideine-2-carboxylic ($\Delta^1$-P2C), and its hydrated form 2-hydroxypiperidine-2-carboxylic acid (P2CH) should be included. Incubation of lysine with L-amino acid oxidase and catalase produced small amounts of 41-P2C and, presumptively, the hydrated product piperidine-2-hydroxy-2-carboxylate (P2H2C). But incubation with lysine oxidase and catalase was far more efficient in producing $\Delta^1$-P2C and P2CH.

Analogous to the $\Delta^2$-P6C/$\Delta^1$-P6C/P6CH equilibrium, the $\Delta^1$-P2C/P2CH equilibrium appeared to change with time favoring one signal, which we assigned as $\Delta^1$-P2C/P2CH mixture. When we incorporate the various components into the method, the resulting $\Delta^1$-P2C/P2CH had a distinctly different retention time from $\Delta^1$-P6C/P6CH, allowing us to monitor metabolites unique for the pipecolate pathway, in addition to saccharopine pathway metabolites.

To evaluate the identified metabolites of the lysine pathway, we expanded the analytic LC/MS-MS method to incorporate lysine, glutamine, AAA, PIP, $\Delta^1$-P2C/P2H2C, $\Delta^2$-P6C, $\Delta^1$-P6C/P6CH, and 6-oxoPIP. There are two peaks for 6-oxo-PIP representing the enol and keto form. For quantification, deuterated d3-AAA and d3-6-oxo-PIP were used as internal standards. The limit of detection (LOD) for $\Delta^1$-P6C/P6CH was 1.0 μM and the limit of quantitation (LOQ) was 2.0 μM. The LOD and LOQ for 6-oxo-PIP were 2.0 mM and 4.0 mM, respectively. A standard curve between 0.5 and 500 μM for quantification of $\Delta^1$-P6C/6-OH-PIP with internal standard d3-AAA had a correlation coefficient >0.99, and for quantification of 6-oxo-PIP with the internal standard d3-6-oxo-PIP had a correlation coefficient >0.985.

Example 6

Human Blood, Blood Spot, CSF and Plasma Samples

In all blood, plasma, and urine samples of subjects affected with PDE we detected AAA, PIP, $\Delta^1$-P6C/P6CH, and 6-oxo-PIP, whereas in samples form 14 control subjects, we only detected AAA and PIP. In two affected subjects, the amount of 6-oxoPIP in urine was 156.8 µmol/mg creatinine and 122.2 µmol/mg creatinine and for $\Delta^1$-P6C/P6CH was 8.5 µmol/mg creatinine and 7.5 µmol/mg creatinine. In plasma, the concentration of 6-oxo-PIP was 2.7±0.1 µM and 4.1±0.1 µM and the concentration of $\Delta^1$-P6C/P6CH was 1.1±0.1 µM and 3.0±0.1 µM for patients 1 and 2, respectively. In CSF from a subject affected with PDE we also identified $\Delta^2$-P6C and a small but clear peak of $\Delta^1$-P2C/P2H2C in addition to $\Delta^1$-P6C/P6CH and 6-oxo-PIP. In three control CSF samples, AAA, and PIP were observed but $\Delta^1$-P6C/P6CH, 6-oxo-PIP, $\Delta^1$-P6C and $\Delta^1$-P2C/P2H2C were absent.

As a primary aim of this research was to evaluate biomarkers suitable for newborn screening, we analyzed blood spots (Whatman 903 Lot W-041) from two subjects and controls. In blood spots stored at room temperature, the signal of $\Delta^1$-P6C/P6CH rapidly degraded over time, and became undetectable after a few days. In contrast, 6-oxo-PIP was noted in the initial blood spot. A freeze-thaw study and a 4-month stability study was done in urine samples from subjects 1 and 2 (Table 4).

loss of $\Delta^1$-P6C/P6CH at $-13\pm3°$ C. and 47-48% loss at $-77\pm3°$ C. The initial 6-oxo-PIP concentrations observed in subject 1 and 2 were 298±23 µM and 440±4 µM, respectively. 6-oxo-PIP showed an initial 20-21% decrease within the first two weeks regardless of storage temperature with, at room temperate, a slower rate of degradation displaying only a 43% and 33% decrease at 126 days for subject 1 and 2, respectively. Thus, at room temperature, 6-oxo-PIP was considerably more stable than $\Delta^1$-P6C/P6CH. Thus, there appears to be potential stability issues with monitoring P6CH/$\Delta^1$-P6C from blood, plasma, and urine while 6-Oxo-PIP appears to be a more stable biomarker.

Example 7

Urine Samples and Urine 4-Month Stability Study

Figure 5:
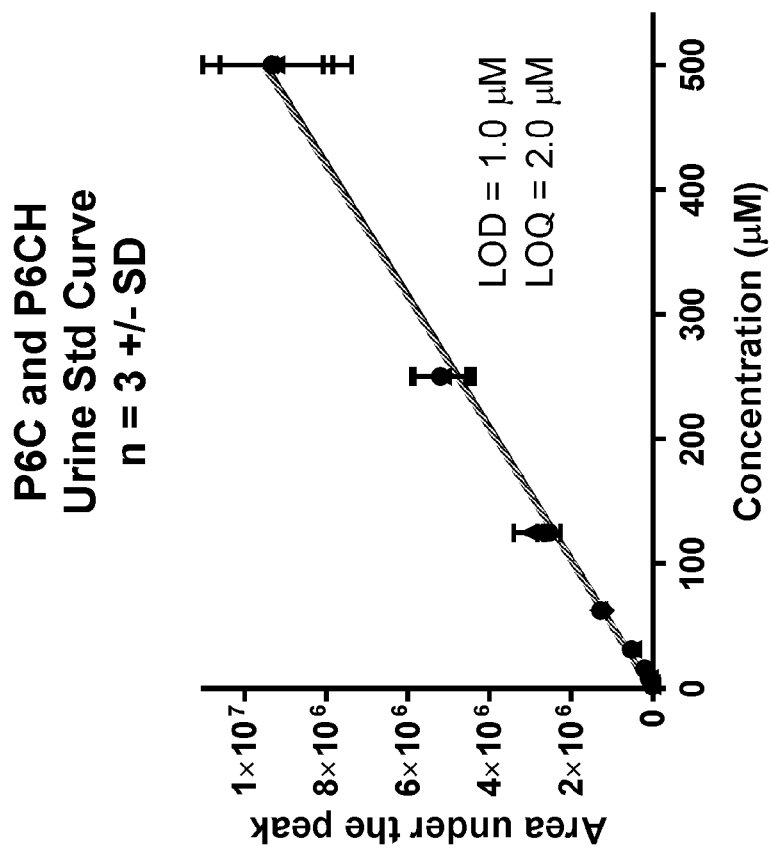
FIG. 5: P6C/P6CH urine standard curves.
Figure 6:
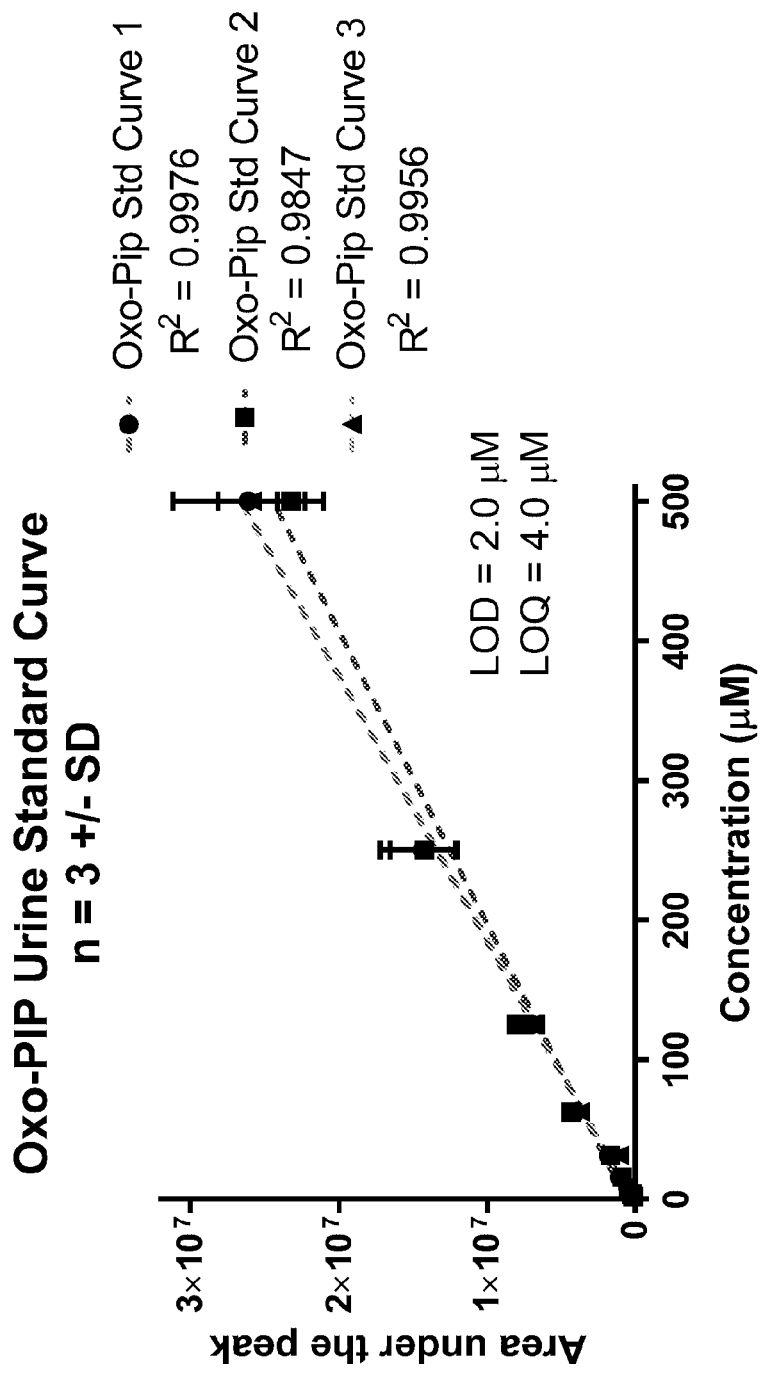
FIG. 6: Oxo-PIP urine standard curves.

Urine samples from two PDE patients exhibited large quantities of 6-Oxo-PIP, in addition to both AAA and $\Delta^1$-P6C/P6CH. To quantify 6-Oxo-PIP and $\Delta^1$-P6C/P6CH, we prepared standard curves ranging from 0.5-500 µM from control urine (FIGS. 5 and 6). In a freeze-thaw study (6-Oxo-PIP, FIG. 6; and P6C/P6CH, FIG. 7) and a 4-month stability study (FIG. 8 and FIG. 9B), fresh urine samples (400 µL) were aliquoted into 1.5 mL Eppendorf tubes and stored either at room temperature (22±2° C.), regular freezer (–13±3° C.) or deep freezer (–77±3° C.) and sampled over a four-month period. First, both biomarkers $\Delta^1$-P6C/P6CH and 6-Oxo-PIP were stable via four freeze-thaw cycles

TABLE 4

Stability study of $\Delta^1$-P6C/P6CH and 6-oxo-PIP

| | Room Temperature | | –15° C. | | –70° C. | |
|---|---|---|---|---|---|---|
| Day (s) | Subject 1 | Subject 2 | Subject 1 | Subject 2 | Subject 1 | Subject 2 |
| V-piperideine-6-carboxyalte ($\Delta^1$-P6C) and 6-hydroxy-pipecolate (P6CH) concentration (µM) | | | | | | |
| 0 | 16 (±1.9) | 27.1 (±2) | | | | |
| 1 | 4.8 (±1.1) | 16.3 (±2.1) | 14.5 (±1.1) | 28.7 (±1.9) | 14.5 (±1.1) | 28.7 (±1.9) |
| 2 | 2.1 (±0.8) | 13.2 (±1.5) | | | | |
| 3 | 1.6 (±0.3) | 7.8 (±0.6) | 15.4 (±0.7) | 25.2 (±1.5) | 13.1 (±0.65) | 27.1 (±0.9) |
| 5 | 0.71 (±0.3) | 5.6 (±1.2) | | | | |
| 7 | (1.54 (±0.21) | 3.0 (±1.1) | 13.6 (±1.3) | 22.1 (±1.6) | 13.2 (±0.5) | 24.2 (±1.3) |
| 10 | 0.32 (±0.18) | 2.5 (±0.82) | 11.7 (±0.8) | 21.3 (±0.9) | 13.5 (±0.76) | 23.0 (±1.5) |
| 14 | 0.13 (±0.02) | 1.3 (±0.24) | 10.5 (±0.4) | 20.1 (±1.4) | 12.9 (±1.6) | 22.6 (±1.1) |
| 21 | 0 | 0.42 (±0.02) | 8.0 (±3.0) | 18.0 (±0.4) | 11.2 (±1.34) | 21.1 (±1.4) |
| 60 | 0 | 0 | 7.2 (±1.8) | 16.4 (±0.7) | 9.7 (±1.4) | 18.2 (±2.3) |
| 126 | 0 | 0 | 5.2 (±1.2) | 13.4 (±0.6) | 7.6 (±1.2) | 15.3 (±2.1) |
| 6-oxo-pipecolate (6-oxo-P1P) concentration (µM) | | | | | | |
| 0 | 297.0 (±23.4) | 440.1 (±4) | 284.8 (±35.7) | 387.6 (±19.1) | 284.8 (±35.7) | 387.6 (±19.1) |
| 1 | 294.8 (±26.4) | 390.8 (±29.3) | | | | |
| 2 | 283.5 (±21.5) | 418.2 (±30.1) | | | | |
| 3 | 30.1 (±20.6) | 387.7 (±55.3) | 243.1 (±12) | 359.0 (±18.2) | 298.2 (±35.1) | 356.4 (±6) |
| 5 | 257.6 (±28.7) | 383.9 (±18.4) | | | | |
| 7 | 252.1 (±11) | 346.0 (±13.5) | 260.8 (±21.8) | 345.0 (+31.1) | 271.9 (+34.4) | 329.2 (±27.2) |
| 10 | 234.7 (±8.9) | 345.2 (±37.6) | 285.1 (±4.7) | 336.5 (±68.9) | 221.7 (±20.3) | 380.3 (±16) |
| 14 | 233.0 (±9.1) | 330.2 (±28.9) | 219.7 (±18.6) | 385.3 (±38.8) | 218.9 (±24.7) | 418.3 (±42.4) |
| 21 | 197.5 (±9.5) | 322.6 (±23.7) | 227.7 (±36.5) | 345.2 (±37.6) | 217.4 (±17.8) | 320.1 (±10.8) |
| 60 | 182.0 (±6.2) | 312.3 (±1.2.8) | 218.4 (±18.3) | 322.3 (±21) | 211.3 (±11.5) | 340.7 (±24.3) |
| 126 | 170.0 (±4) | 295.3 (±21.4) | 211.5 (±9.4) | 314.3 (±17.4) | 198.4 (±8.7) | 322.7 (±35) |

Legend: $\Delta^1$-P6C/6-OH-PIP and of 6-oxo-PIP were quantified in urine samples from two subjects with pyridoxine-dependent epilepsy. Samples were tested at room temperature, –15° C., and –70° C. between 0 and 126 days from date of sample collection. Samples were run in triplicate and concentration was reported as the mean + standard deviation.

The original concentrations of $\Delta^1$-P6C/P6CH for subject 1 and 2 were 16.1±1.9 µM and 27.1±2.0 µM, respectively. At room temperature, $\Delta^1$-P6C/P6CH degraded within a couple of days with only trace amounts remaining after two weeks. When in the freezer or the deep freezer, $\Delta^1$-P6C/P6CH decayed moderately. After 126 days, there was a 53-64%

Figure 7:
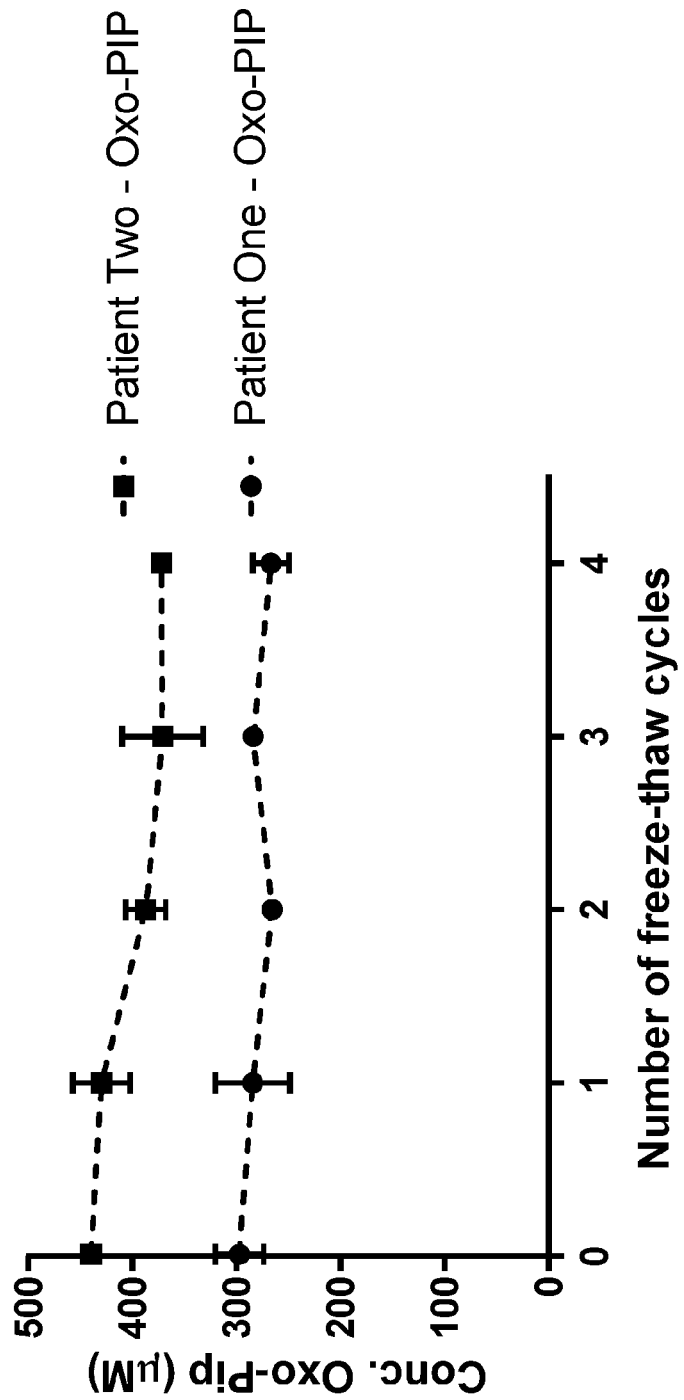
FIG. 7: Oxo-PIP four freeze-thaw cycle stability.
Figure 8:
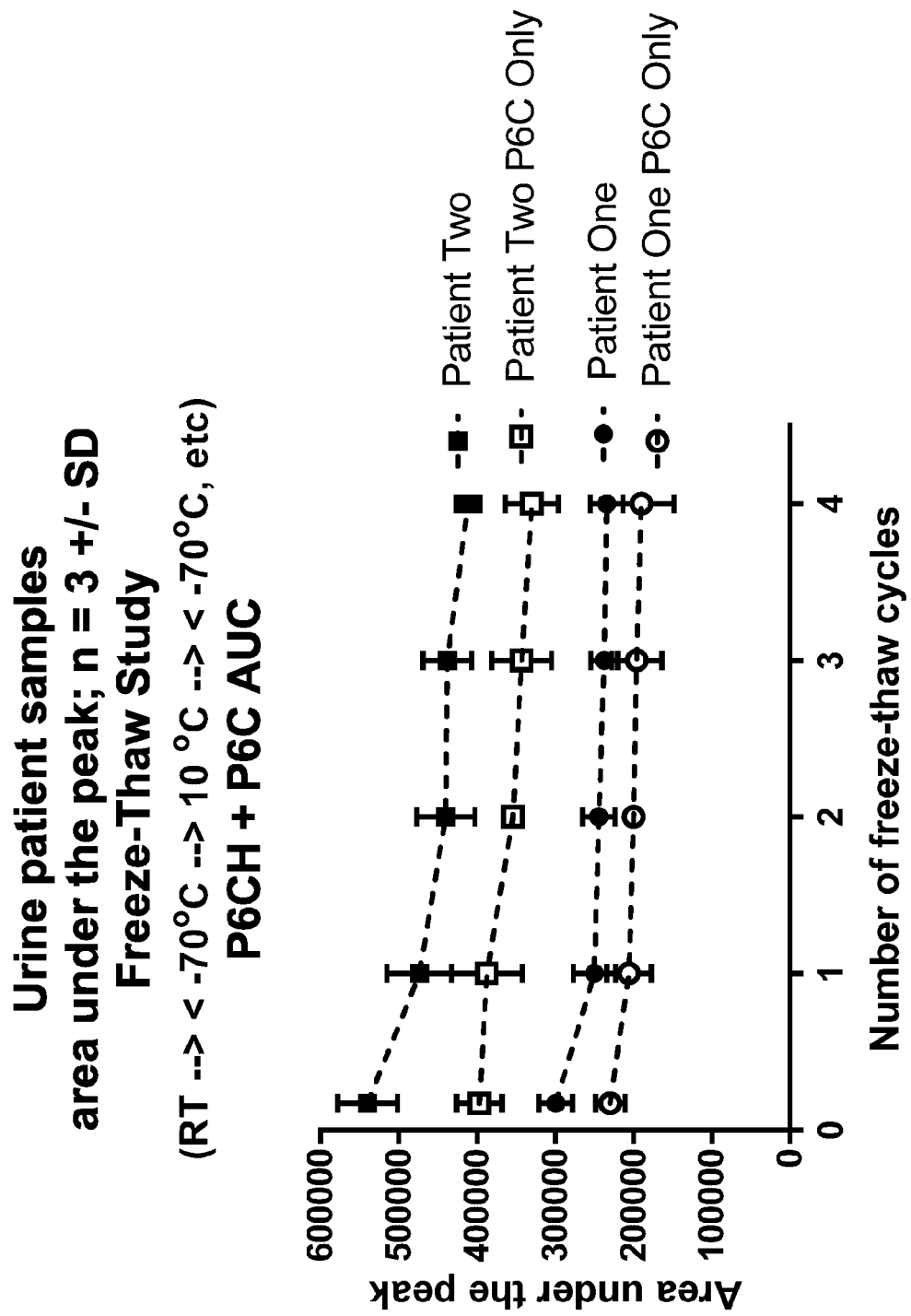
FIG. 8: P6CH and P6C four freeze-thaw cycle stability.
Figure 9:
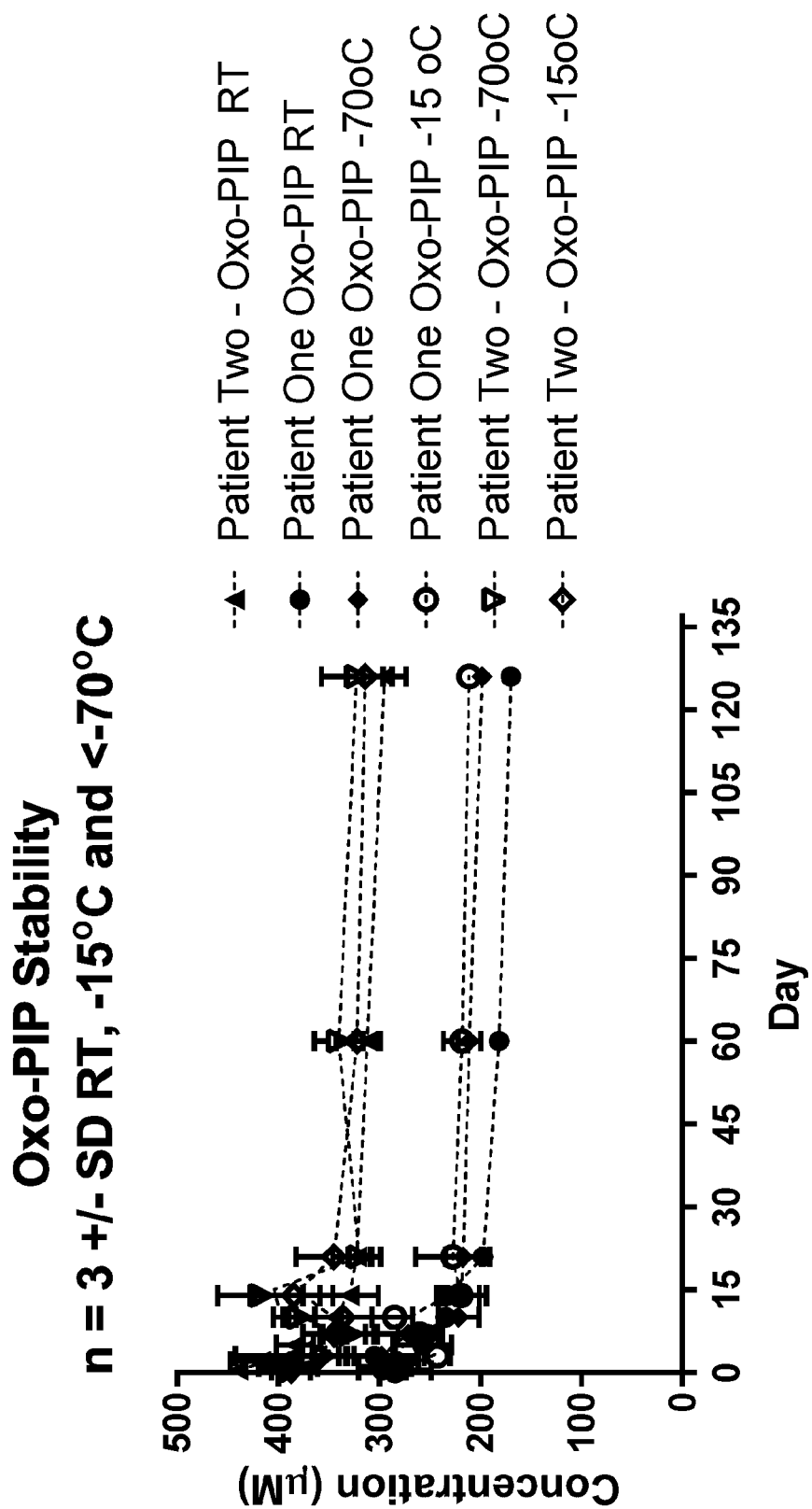
FIG. 9: Oxo-PIP temperature stability study summary.
Figure 10A:
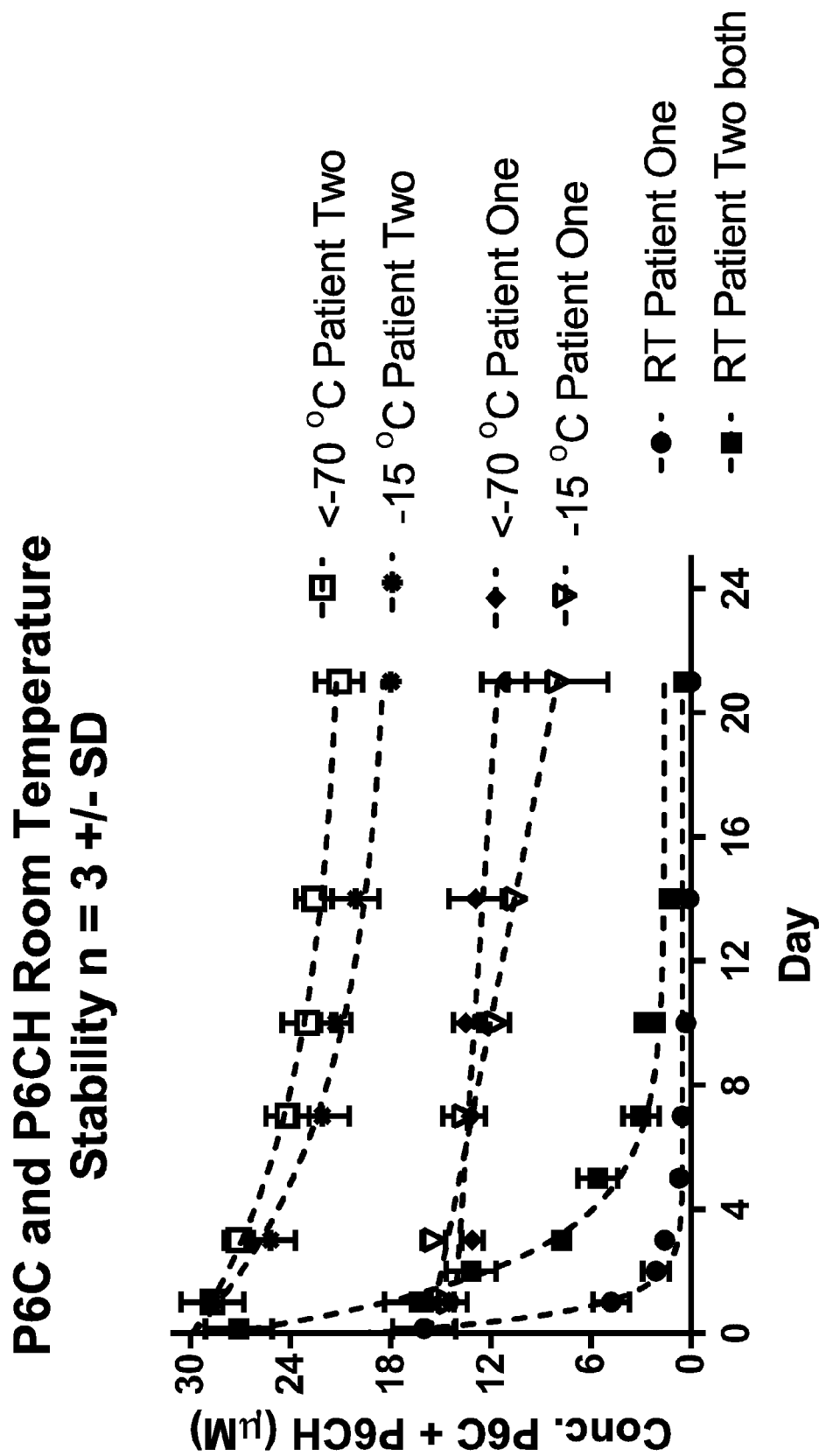
FIGS. 10A and 10B: show data summaries of P6C/P6CH temperature stability studies.
Figure 10B:
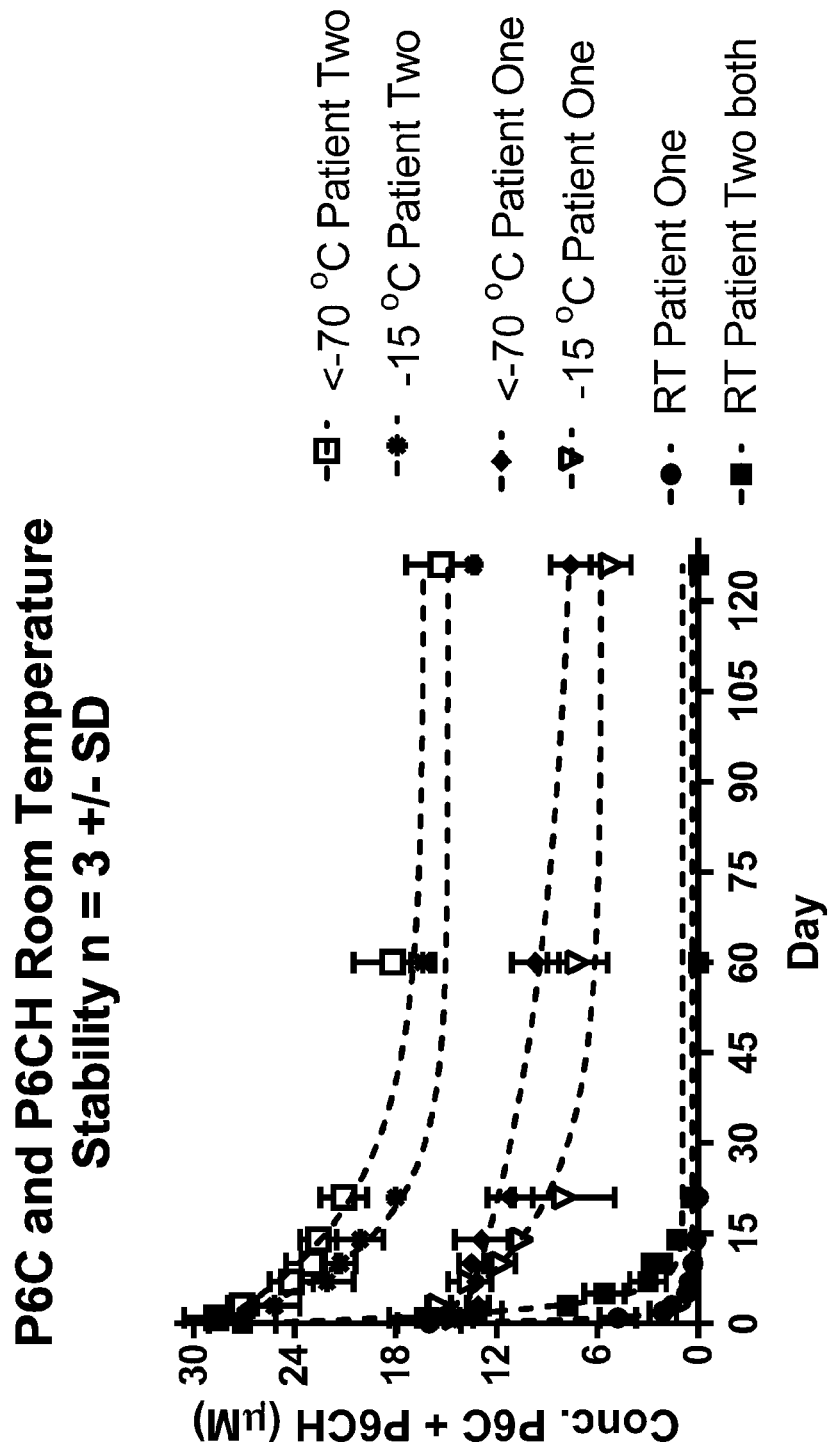

(6-Oxo-PIP FIG. 6; and $\Delta^1$-P6C/P6CH FIG. 7). The initial 6-Oxo-PIP concentrations observed with patient one and patient two were 298±23 and 440±4 µM, respectively. 6-Oxo-PIP showed an initial 20-21% decrease within the first two weeks regardless of storage temperature with a slower rate of degradation displaying 33% and 43% decrease at 126 days for patient two and one, respectively (FIG. 8). In contrast, $\Delta^1$-P6C/P6CH (FIG. 9B) was less stable. The original concentrations of $\Delta^1$-P6C/P6CH for patient one and two were 16.1±1.9 µM and 27.1±2.0 µM, respectively, an order of magnitude less than 6-oxo-PIP. At room temperature, $\Delta^1$-P6C/P6CH degraded within a couple of days (FIG. 9A) with only trace amounts remaining after two weeks. When in the freezer or the deep freezer, $\Delta^1$-P6C/P6CH displayed moderate stability with a 53-64% loss of $\Delta^1$-P6C/P6CH at −13±3° C. and 47-48% loss at −77±3C. Even after 126 days storage, roughly half of the $\Delta^1$-P6C/P6CH from the original sample (day 1) remained. Thus, when kept in deep frozen state, there was only a limited difference in the stability of both biomarkers, but at room temperature, 6-oxo-PIP was considerably more stable than $\Delta^1$-P6C/P6CH.

We also utilized D3-AAA and D3-6-Oxo-PIP as internal standards. The limit of detection (LOD) for $\Delta^1$-P6C/P6CH (FIG. 5) was 1.0 µM and the limit of quantitation (LOQ) was 2.0 µM, while for 6-Oxo-PIP (FIG. 6) the LOD and LOQ were 2.0 µM and 4.0 µM, respectively. The amount of 6-oxo-PIP in these urine samples was 156.8 and 122.2 µmol/mg creatinine and for $\Delta^1$-P6C/P6CH was 8.5 and 7.5 µmol/mg creatinine for patient 1 and 2 respectively.

Example 8

CSF Samples

Lastly, CSF samples (control and PDE subject sample) were analyzed to illustrate that control CSF was very different as compared to patient sample. The control samples only showed lysine and an unknown, whereas the PDE patient CSF sample showed $\Delta^1$-P6C/P6CH, 6-oxo-PIP, and evidence for $\Delta^2$-P6C and a small but clear peak of $\Delta^1$-P2C/P2CH, in addition to degradation products and some unknown peaks. In contrast to plasma, CSF also showed metabolites unique to the pipecolate pathway, although relative quantity of the flux from both pathways cannot be deduced from this study, these data support the notion that the saccharopine pathway (P6C/P6CH) predominates in human brain.

These results describe a novel biomarker (6-oxo-PIP) for PDE, which has significant implications for newborn screening of this treatable disease. Previous attempts at newborn screening were limited as the primary biomarkers, $\Delta^1$-P6C and α-AASA, degraded rapidly at room temperature (Jung et al. 2013, Mol Genet Metab 110:237-40; Mathew et al. 2018, Int J Anal Chem 2583215). Our results show that 6-oxo-PIP was measurable for up to four months in urine samples stored at room temperature. Stability at room temperature is essential as the current newborn screening paradigm relies on samples to be collected, dried, and shipped at room temperature. Using a stable isotope-labeled internal standard, we developed a non-derivatized method LC-MS/MS based method to quantify 6-oxoPIP in subjects and controls. We suggest that screening for PDE could be added to the current newborn screen paradigm where samples are collected on filter paper cards, dried and shipped at room temperature, and analyzed via non-derivatized MS/MS analytical methods. To our knowledge, 6-oxo-PIP has not been reported in patients with PDE or other defects of lysine metabolism, although it has been identified in *Penicillium chrysogenum* (Brundidge et al. 1980, J Antibiot 33:1348-1351; Henriksen et al. 1998, J Antibiot 51:99-106).

The presence of 6-oxo-PIP was suggested by the presence of 6-OH-PIP as an intermediate step between $\Delta^1$-P6C and α-AASA (FIG. 4). 6-OH-PIP represents the cyclization of α-AASA without loss of water and the simple addition of water across the C=N bond in $\Delta^1$-P6C. Oxidation of the secondary alcohol in 6-OH-PIP results in the formation 6-oxo-PIP. Our combined NMR, mass spectrometry and DNP reactivity data suggests that a mixture of $\Delta^1$P6C/P6CH exists, although this mixture could not be separated despite the use of multiple analytical methods. We suggest that these two metabolites are in a very rapid equilibrium in any aqueous condition. The initial NMR experiments are consistent with both a double bond and a hydroxyl group. This suggests that both interacting products are present in the original standard and not solely occurring with the analytical mass spectrometry method.

Various mutations in ALDH7A1 result in the accumulation of $\Delta^1$-P6C/P6CH and α-AASA. αAASA dehydrogenase is present in both mitochondria and cytosol. When $\Delta^1$-P6C/P6CH accumulates, it appears to be a substrate of a dehydrogenase using NAD+ located in the cytosol, but not in the mitochondria, and resulting in the formation of 6-oxo-PIP. An alternative possibility includes the formation of pipecolate from the incubated $\Delta^1$-P6C and a direct oxidation of pipecolate to 6-oxo-PIP, although this appears less likely. The 6-oxo-PIP formed cannot be further metabolized to AAA and accumulates in patients with PDE.

Of note, we identified a small but distinct peak of $\Delta^1$-P2C/P2H2C in the CSF of a single affected subject, which was not identified in blood, plasma or urine of affected patients. The presence of $\Delta^1$-P2C/P2H2C may indicate a role for the pipecolate pathway in human brain lysine metabolism.

In conclusion, we have identified 6-OH-PIP as an intermediate metabolite between $\Delta^1$-P6C and α-AASA in lysine oxidation. A minor cytosolic enzymatic pathway allows oxidation to 6-oxo-PIP. Accumulation of 6-oxo-PIP was identified in the blood, plasma, urine and CSF of subjects with PDE and represents a novel biomarker. This disclosure presents an analytical method for quantification of this new biomarker using stable isotope dilution of LC-MS/MS. Unlike previously identified biomarkers for PDE, 6-oxo-PIP was relatively stable at room temperature. Stability of a biomarker at room temperature is essential to add screening for PDE into existing newborn screening paradigms.

The contents of the articles, patents, patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A method of screening for pyridoxine dependent epilepsy (PDE) in a subject, the method comprising:
    collecting a sample from the subject, wherein the sample is stable at room temperature for up to four months;
    adding deuterated 6-oxopipecolic acid (Oxo-PIP) as an internal standard to the sample;
    detecting whether Oxo-PIP is present in the sample by mass spectrometry; and
    quantifying the amount of Oxo-PIP in the sample if Oxo-PIP is present in the sample,
    wherein the subject is identified as having PDE when the amount of Oxo-PIP in the sample is greater than a threshold value.

2. The method of claim 1, wherein at least 80% of Oxo-PIP in the sample remains after two weeks.

3. The method of claim 1, wherein at least 55% of Oxo-PIP in the sample remains after four months.

4. The method of claim 1, wherein the subject is a newborn human.

5. The method of claim 1, wherein the sample is a biological fluid selected from saliva, sweat, urine, blood, serum, plasma, cerebrospinal fluid (CSF), and combinations thereof.

6. The method of claim 1, wherein the sample is collected on filter paper, dried, and shipped at room temperature to a facility for mass spectrometry analysis.

7. The method of claim 1, wherein the mass spectrometry is liquid chromatography tandem mass spectrometry (LC/MS-MS).

8. The method of claim 7, wherein the transitions for Oxo-PIP in mass spectra from LC/MS-MS are at 144.2 to 98.1.

9. A method of diagnosing and treating pyridoxine dependent epilepsy (PDE) in a subject, the method comprising:
    diagnosing PDE in the subject by:
        collecting a sample from the subject, wherein the sample is stable at room temperature for up to four months;
        subjecting the sample to mass spectrometric analysis using deuterated 6-oxopipecolic acid (Oxo-PIP) as an internal standard; and
        diagnosing PDE in the subject if Oxo-PIP is detected in the sample above a threshold value; and
    treating PDE by at least one of administering an effective amount of vitamin B6 to the subject, administering an effective amount of pyridoxine to the subject, or restricting dietary lysine of the subject.

10. The method of claim 9, wherein at least 80% of Oxo-PIP in the sample remains after two weeks.

11. The method of claim 9, wherein at least 55% of Oxo-PIP in the sample remains after four months.

* * * * *